US007619070B2

(12) United States Patent
Cardarelli et al.

(10) Patent No.: US 7,619,070 B2
(45) Date of Patent: Nov. 17, 2009

(54) HUMANIZED ANTIBODIES TO INTERFERON ALPHA RECEPTOR-1 (IFNAR-1)

(75) Inventors: Josephine M. Cardarelli, San Carlos, CA (US); Tseng-Hui Timothy Chen, Burlingame, CA (US); David J. King, Belmont, CA (US); Christopher R. Bebbington, San Mateo, CA (US); Sarah Lee Pogue, Fremont, CA (US); Francis J. Carr, Aberdeenshire (GB); Stephen Williams, Aberdeenshire (GB)

(73) Assignee: Medarex, Inc., Princeton, NJ (US)

( * ) Notice: Subject to any disclaimer, the term of this patent is extended or adjusted under 35 U.S.C. 154(b) by 0 days.

(21) Appl. No.: 10/831,459

(22) Filed: Apr. 23, 2004

(65) Prior Publication Data

US 2005/0208041 A1 Sep. 22, 2005

Related U.S. Application Data

(60) Provisional application No. 60/465,058, filed on Apr. 23, 2003.

(51) Int. Cl.
*C12P 21/08* (2006.01)
(52) U.S. Cl. .............................. 530/387.3; 530/388.22
(58) Field of Classification Search ........................ None
See application file for complete search history.

(56) References Cited

U.S. PATENT DOCUMENTS

| | | | |
|---|---|---|---|
| 4,816,567 A | 3/1989 | Cabilly et al. | |
| 5,693,762 A | 12/1997 | Queen et al. | |
| 5,886,153 A | 3/1999 | Mogensen et al. | |
| 5,919,453 A | 7/1999 | Benoit et al. | |
| 6,787,634 B2 | 9/2004 | Benoit et al. | |
| 2002/0055492 A1* | 5/2002 | Benoit et al. | 514/100 |

FOREIGN PATENT DOCUMENTS

| | | | |
|---|---|---|---|
| EP | 0 563 487 A | | 10/1993 |
| WO | WO 9007861 A1 * | | 7/1990 |
| WO | WO-95/07716 A | | 3/1995 |
| WO | WO 9852976 A1 * | | 11/1998 |
| WO | WO-01/54721 A | | 8/2001 |
| WO | WO-01/55215 A | | 8/2001 |

OTHER PUBLICATIONS

Janeway et al., Immunobiology, p. 3.2, Garland Publishing, New York, 1997.*
Rudikoff, et al. Proc. Natl. Acad. Sci. USA 79: 1979-83 (1982).*
Wu et al., J. Mol. Biol. 294: 151-162 (1999).*
Paul, Fundamental Immunology, 3rd Ed., pp. 292-295, Raven Press, New York, 1993.*
Reff et al., Crit. Rev. Oncol. Hematol. 40: 25-35 (2001).*
MacCallum et al, J. Mol. Biol., 262,732-745, 1996.*
Brown et al., J Immunol. May 1, 1996;156(9):3285-91.*
Casset et al, Biochemical and Biophysical Research Communications, 307:198-205, 2003.*
Mateo et al., Hybridoma. Dec. 2000;19(6):463-71.*
Deavin et al., Mol Immunol. Feb. 1996;33(2):145-55.*
Janeway et al., Immunobiology, 5th Ed., Garland Science, pp. 116-117 (2001).*
Vajdos et al., J Mol Biol. Jul. 5, 2002;320(2):415-28.*
Colman P. M., Research in Immunology, 145:33-36, 1994.*
Amin et al., Innovations in Pharmaceutical Technology, Samedan Ltd, publishers, Jun. 2002.*
O'Brien et al., Humanization of Monoclonal Antibodies by CDR Grafting, Methods in Molecular Biology, Humana Press, 2003, pp. 81-100.*
The Declaration under 37 C.F.R. § 1.132 of Dr. Michael G. Tovey, May 9, 2002, pp. 1-8 published in conjunction with the publication of US 20020055492.*
Aguet et al., "Interferon 5" Ed. I. Gresser p. 1-22, Academic Press, London 1983.
Arvin and Miller, Arthritis Rheum. 1984;27:582-585.
Brinkmann et al., J. Exp. Med., 1993;178:1655-1663.
Cook et al., J. Biol. Chem. 1996;271:13448-13453.
Cutrone and Langer, J. Biol. Chem. 2001;276:17140-17148.
Finkelman et al., J. Exp. Med. 1991;174:1179-1188.
Foulis et al., Lancet. 1987;2:1423-1427.
Haller et al., J. Exp. Med. 1981;154:199-203.
Hardy et al., Blood. 2001;97:473-482.
Hertzog et al., Clin Immunol. Immunopath. 1988;48:192-201.
Hooks et al., Arthritis Theum/ 1982;25:396-400.
Hopkins and Meager, Clin. Exp. Immunol. 1988;73:88-92.
Lewerenz et al., J. Mol. Biol. 1998;282:585-599.
Lindenmann et al., Methods Enzymol. 1981;78:181-188.
Luft et al., J. Immunol. 1998;161:1947-1953.
Luft et al., Int. Immunol. 2002;14:367-380.
Radvanyi et al., Scan. J. Immunol. 1999+:50:499-509.
Santini et al., J. Exp. Med. 2000;191:17771788.
Streuli et al., PNAS-USA. 1981;78:2848-2852.
Tough et al., Science. 1996;272:1947-1950.
Benoit et al., "A Monoclonal Antibody to Recombinant Human IFN-α Receptor Inhibits Biologic Activity of Several Species of Human IFN-α, IFN-β, and IFN-Ω. Detection of Heterogeneity of the Cellular Type I IFN Receptor," *Journal of Immunology*, 150:707-716 (1993).
Blanco et al., "Induction of Dendritic Cell Differentiation by IFN-α in Systemic Lupus Erythematosus," Science, *American Association for the Advancement of Science*, 294:1540-1543 (2001).
Corssmit et al., "Effects of Interferon-α (INF-α) Administration on Leucocytes in Healthy Humans," *Clinical and Experimental Immunology*, 107:359-363 (1997).
Eid et al., "Localization of a Receptor Nonapeptide with a Possible Role in the Bindign of the Type I Interferons," *European Cytokine Network*, 11:560-573 (2000).
Tilg et al., "Interferon-α Induces Circulating Tumor Necrosis Factor Receptor p55 in Humans," *Blood*, 85:433-435 (1995).

(Continued)

*Primary Examiner*—Ram R Shukla
*Assistant Examiner*—Zachary Skelding
(74) *Attorney, Agent, or Firm*—Baker Botts L.L.P.

(57) ABSTRACT

Humanized monoclonal antibodies which bind to IFNAR-1, and related antibody-based compositions and molecules, are disclosed. Also disclosed are pharmaceutical compositions comprising the humanized antibodies and therapeutic and diagnostic methods for using the humanized antibodies.

17 Claims, 11 Drawing Sheets

OTHER PUBLICATIONS

Winter et al., "Humanized Antibodies," *Trends in Pharmacological Sciences*, 14:139-143 (1993).

Soderlind et al., "The immune diversity in a test tube—non-immunised antibody libraries and functional variability in defined protein scaffolds," Comb Chem High Throughput Screen. Aug. 2001;4(5):409-16.

Klimka et al., "Human anti-CD30 recombinant antibodies by guided phage antibody selection using cell panning," Br J Cancer. Jul. 2000;83(2):252-60.

Marks et al., "By-passing immunization: building high affinity human antibodies by chain shuffling," Biotechnology (N Y). Jul. 1992;10(7):779-83.

Rader et al., "A phage display approach for rapid antibody humanization: designed combinatorial V gene libraries," Proc Natl Acad Sci U S A. Jul. 21, 1998;95(15):8910-5.

Yang et al., "CDR walking mutagenesis for the affinity maturation of a potent human anti-HIV-1 antibody into the picomolar range," J Mol Biol. Dec. 1, 1995;254(3):392-403.

Barbas et al., "In vitro evolution of a neutralizing human antibody to human immunodeficiency virus type 1 to enhance affinity and broaden strain cross-reactivity," Proc Natl Acad Sci U S A. Apr 26, 1994;91(9):3809-13.

Wu et al., "Stepwise in vitro affinity maturation of Vitaxin, an alphav beta3-specific humanized mAb," Proc Natl Acad Sci U S A. May 26, 1998;95(11):6037-42.

Mogensen, et al., "The Type I Interferon Receptor: Structure, Function and Evolution of a Family Business," *J. of Interferon and Cytokine Research* (1999); 19: 1069-1098.

Kettleborough, et al., "Humanization of a Mouse Monoclonal Antibody by CDR-grafting: the Importance of Framework Residues on Loop Conformation," *Protein Engineering* (1991); 4(7): 773-783.

Benoit, et al., A Monoclonal Antibody to Recombinant Human INF-$\alpha$ Receptor Inhibits Biologic Activity of Several Species of Human IFN-$\alpha$, IFN-$\beta$, and IFN-$\omega$, J Immunology, 150(3):707-716 (1993).

Eid et al., "Characterization of a Domain of Human Type I Interferon Receptor Protein Involved in Ligand Binding", J. Interferon Cytokine Research, 15:205-211 (1995).

* cited by examiner

FIG. 1A: 64G12 VH

QVTLKESGPGILKPSQTLSLTCSFSGFSLSTSGMGIGWIRQPSGKGLEWLAHIWWDDDKYYNPSLKSQLTISRDTST
NQVFLNITSVDTVDTATYYCGRNYYPYDAWFDYWGQGTLVTVS (SEQ ID NO:7)

FIG. 1B: H2

QVTLKESGPALVKPTQTLTLTCTFSGFSLSTSGMGIGWIRQPPGKALEWLAHIWWDDDKYYNPSLKSRLTISRDTSK
NQVVLTMTMDPVDTATYYCGRNYYPYDAWFDYWGQGTLVTVS (SEQ ID NO:8)

FIG. 1C: H2-C3

QVTLKESGPALVKPTQTLTLTCTFSGFSLSTSGMRVSWIRQPPGKALEWLARIDWDDDKFYSTSLKTRLTISRDTSK
NQVVLTMTMDPVDTATYYCGRNYYPYDAWFDYWGQGTLVTVS (SEQ ID NO:9)

FIG. 1D: H3

EVQLVESGGGLVQPGGSLRLSCAFSGFTLSTSGMGIGWVRQAPGKGLEWVAHIWWDDDKYYNPSLKSRFTISRDT
SKNTVYLQMNSLRAEDTAVYYCARNYYPYDAWFDYWGQGTLVTVS (SEQ ID NO:10)

FIG. 1E: M3

EVQLLESGGGLVQPGGSLRLSCAFSGFTLSTSGMGIGWVRQAPGKGLEWVAHIWWDDDKYYNPSLKSRFTISRDT
SKNTVYLQMNSLRAEDTAVYYCARNYYPYDAWFDYWGQGTLVTVS (SEQ ID NO:11)

FIG. 1F: M3-4

EVQLLESGGGLVQPGGSLRLSCAFSGFTLSTSGMGIGWVRQAPGKGLEWVAHIWWDDDKYYNPSLKSRFTISRDT
SKNTVYLQMNSLRAEDTAVYYCARNYXXYDAWFDYWGQGTLVTVS (SEQ ID NO:12)

FIG. 1G: M3-11

EVQLLESGGGLVQPGGSLRLSCAFSGFTLSTSGMGIGWVRQAPGKGLEWVAHIWWDDDKYYNPSLKSRFTISRDT
SKNTVYLQMNSLRAEDTAVYYCARNYYPYDAWFDXWGQGTLVTVS (SEQ ID NO:13)

FIG 1H: M3-A

EVQLLESGGGLVQPGGSLRLSCAFSGFTLSTSGAGIGWVRQAPGKGLEWVAHIWWDDDKYYNPSLKSRFTISRDTS
KNTVYLQMNSLRAEDTAVYYCARNYYPPYDAWFDYWGQGTLVTVS (SEQ ID NO:14)

FIG 1I: M3-B

EVQLLESGGGLVQPGGSLRLSCAFSGFTLSTSGMGIGWVRQAPGKGLEWVAHIWWDDDKYYNPSLKARFTISRDT
SKNTVYLQMNSLRAEDTAVYYCARNYYPPYDAWFDYWGQGTLVTVS (SEQ ID NO:15)

FIG. 1J: M3-A/B

EVQLLESGGGLVQPGGSLRLSCAFSGFTLSTSGAGIGWVRQAPGKGLEWVAHIWWDDDKYYNPSLKARFTISRDTS
KNTVYLQMNSLRAEDTAVYYCARNYYPPYDAWFDYWGQGTLVTVS (SEQ ID NO:16)

FIG. 1K: DI M3

EVQLLESGGGLVQPGGSLRLSCAASGFTMSTSGMGIGWIRQTPGKGLEWVAHIWWDDDKYYNPSLKSRFTISKDT
SKNTLYLQMNSLRAEDTAVYYCARNYYPYDAWFDYWGQGTLVTVS (SEQ ID NO:17)

FIG. 1L: DI M3-B

EVQLLESGGGLVQPGGSLRLSCAASGFTMSTSGMGIGWIRQTPGKGLEWVAHIWWDDDKYYNPSLKARFTISRDT
SKNTLYLQMNSLRAEDTAVYYCARNYYPYDAWFDYWGQGTLVTVS (SEQ ID NO:18)

FIG. 2A: 64G12 VL

EIVLTQSPTTMAASPGEKITITCSASSSINSNHLHWYQQKPGFSPKVLIYRTSILASGVPTRFSGSGSGTSYSLTIGTM
EAEDVATYYCQQGSNIPFTFGSGTELEIKR (SEQ ID NO:19)

FIG. 2B: K6

EIVLTQSPDFQSVTPKEKVTITCSASSSINSNHLHWYQQKPGQSPKLLIYRTSILASGVPSRFSGSGSGTSFTLTINSL
EAEDVATYYCQQGSNIPFTFGQGTKLEIKR (SEQ ID NO:20)

FIG. 2C: K1

DIQMTQSPSSLSASVGDRVTITCSASSSINSNHLHWYQQKPGKAPKLLIYRTSILASGVPSRFSGSGSGTSFTLTISS
LQPEDFATYYCQQGSNIPFTFGQGTKVEIKR (SEQ ID NO:21)

FIG. 2D: K1-C

DIQMTQSPSSLSASVGDRVTITCSASTSINSNHLHWYQQKPGKAPKLLIYRTSILASGVPSRFSGSGSGTSFTLTISS
LQPEDFATYYCQQGSNIPFTFGQGTKVEIKR (SEQ ID NO:22)

FIG. 2E: K1-D

DIQMTQSPSSLSASVGDRVTITCSASSSINSNHLMWYQQKPGKAPKLLIYRTSILASGVPSRFSGSGSGTSFTLTISS
LQPEDFATYYCQQGSNIPFTFGQGTKVEIKR (SEQ ID NO:23)

FIG. 2F: K1-E

DIQMTQSPSSLSASVGDRVTITCSASSSINSNHLHWYQQKPGKAPKLLIYRTSILASGVPSRFSGSGSGTSFTLTISS
LQPEDFATYYCQQTSNIPFTFGQGTKVEIKR (SEQ ID NO:24)

FIG. 2G: K1-C/D

DIQMTQSPSSLSASVGDRVTITCSASTSINSNHLWYQQKPGKAPKLLIYRTSILASGVPSRFSGSGSGTSFTLTISS
LQPEDFATYYCQQGSNIPFTFGQGTKVEIKR (SEQ ID NO:25)

FIG. 2H: K1-C/E

DIQMTQSPSSLSASVGDRVTITCSASTSINSNHLWYQQKPGKAPKLLIYRTSILASGVPSRFSGSGSGTSFTLTISS
LQPEDFATYYCQQTSNIPFTFGQGTKVEIKR (SEQ ID NO:26)

FIG. 2I: K1-D/E

DIQMTQSPSSLSASVGDRVTITCSASSSINSNHLWYQQKPGKAPKLLIYRTSILASGVPSRFSGSGSGTSFTLTISS
LQPEDFATYYCQQTSNIPFTFGQGTKVEIKR (SEQ ID NO:27)

FIG. 2J: K1-C/D/E

DIQMTQSPSSLSASVGDRVTITCSASTSINSNHLWYQQKPGKAPKLLIYRTSILASGVPSRFSGSGSGTSFTLTISS
LQPEDFATYYCQQTSNIPFTFGQGTKVEIKR (SEQ ID NO:28)

FIG. 2K: DI K1

DIQMTQSPSSLSASVGDRATITCSASSSINSNHLHWYLQKPGKAPKALIYRTSILASGIPSRFSGSGSGTDFTLTISSL
QPEDTATYYCQQGSNIPFTFGQGTKVEIKRTVAAP (SEQ ID NO:29)

FIG. 2L: DI K1-C

DIQMTQSPSSLSASVGDRVTITCSASTSINSNHLHWYLQKPGKAPKALIYRTSILASGIPSRFSGSGSGTDFTLTISSL
QPEDTATYYCQQGSNIPFTFGQGTKVEIKRTVAAP (SEQ ID NO:30)

FIG. 2M: DI K1-DS

DIQMTQSPSSLSASVGDRATITCSASSSINSNHLHWYLQKPGKAPKALIYRTSILASGIPSRFSGSGSGTSFLTISSL
QPEDTATYYCQQGSNIPFTFGQGTKVEIKRTVAAP (SEQ ID NO:31)

FIG. 2N: DI K1-C-DS

DIQMTQSPSSLSASVGDRVTITCSASTSINSNHLHWYLQKPGKAPKALIYRTSILASGIPSRFSGSGSGTSFLTISSL
QPEDTATYYCQQGSNIPFTFGQGTKVEIKRTVAAP (SEQ ID NO:32)

FIG. 2O: DI K1-A19V

DIQMTQSPSSLSASVGDRVTITCSASSSINSNHLHWYLQKPGKAPKALIYRTSILASGIPSRFSGSGSGTDFTLTISSL
QPEDTATYYCQQGSNIPFTFGQGTKVEIKRTVAAP (SEQ ID NO:33)

FIG. 2P: DI K1-L37Q

DIQMTQSPSSLSASVGDRATITCSASSSINSNHLHWYQQKPGKAPKALIYRTSILASGIPSRFSGSGSGTDFTLTISS
LQPEDTATYYCQQGSNIPFTFGQGTKVEIKRTVAAP  (SEQ ID NO:34)

FIG. 2Q: DI K1-A46L

DIQMTQSPSSLSASVGDRATITCSASSSINSNHLHWYLQKPGKAPKLLIYRTSILASGIPSRFSGSGSGTDFTLTISSL
QPEDTATYYCQQGSNIPFTFGQGTKVEIKRTVAAP  (SEQ ID NO:35)

FIG. 2R: DI K1-I58V

DIQMTQSPSSLSASVGDRATITCSASSSINSNHLHWYLQKPGKAPKALIYRTSILASGVPSRFSGSGSGTDFTLTISS
LQPEDTATYYCQQGSNIPFTFGQGTKVEIKRTVAAP  (SEQ ID NO:36)

FIG. 2S: DI K1-T83F

DIQMTQSPSSLSASVGDRATITCSASSSINSNHLHWYLQKPGKAPKALIYRTSILASGIPSRFSGSGSGTDFTLTISSL
QPEDFATYYCQQGSNIPFTFGQGTKVEIKRTVAAP  (SEQ ID NO:37)

FIG. 3A: M3 gaggtgcagctgttggagtctgggggaggcttggtacagcctggggggtccctgagactctcctgtgcattct
ccggattcaccctgagcacttctggtatgggtataggctgggtccgccaggctcccgggaaggggctggag
tgggtcgcacacatttggtgggatgatgataagtactataatccatccctgaagagtcggttcaccatctcca
gagacacttccaagaacacggtatatctgcaaatgaacagcctgagagccgaggacactgcagtatatta
ctgtgcgagaaattactatccttacgacgcctggtttgactactggggtcaaggtaccctagtcaccgtctca
(SEQ ID NO:38)

FIG. 3B: K1 gatatccagatgacccagtccccgagctccctgtccgcctctgtgggcgatagggtcaccatcacctgcagt
gccagctcaagtataaattccaatcacttacactggtatcaacagaaaccaggaaaggcgccgaaactgc
tgatttacaggacatccattctggcttctggagtcccttctcgcttctctggttccggatctgggacgtctttcactct
gaccatcagctccctgcagccggaagacttcgcaacttattactgtcagcagggtagtaatatcccattcact
ttcggacagggtaccaaggtggagatcaaacgt (SEQ ID NO:39)

FIG. 3C: DI M3-B gaggtgcagctgttggagtctgggggaggcttggtacagcctggggggtccctgagactctcctgtgcagc
ctccggcttcaccatgagcacttccggaatgggtataggctggatccgccagaccccgggaaggggctc
gagtgggtcgcacacatttggtgggatgatgataagtactataatccatccctgaaggctagattcaccatct
ccagagacacttccaagaacacgctgtatctgcaaatgaacagcctgagagccgaggacactgcagtat
attactgtgcgagaaattactatccttacgacgcctggtttgactactggggtcaaggtaccctagtcaccgtct
ca (SEQ ID NO:40)

FIG. 3D: K1-C gatatccagatgacccagtccccgagctccctgtccgcctctgtgggcgatagggtcaccatcacctgcagt
gccagcacaagtataaattccaatcacttacactggtatcaacagaaaccaggaaaggcgccgaaactg
ctgatttacaggacatccattctggcttctggagtcccttctcgcttctctggttccggatctgggacgtctttcact
ctgaccatcagctccctgcagccggaagacttcgcaacttattactgtcagcagggtagtaatatcccattca
ctttcggacagggtaccaaggtggagatcaaacgt (SEQ ID NO:41)

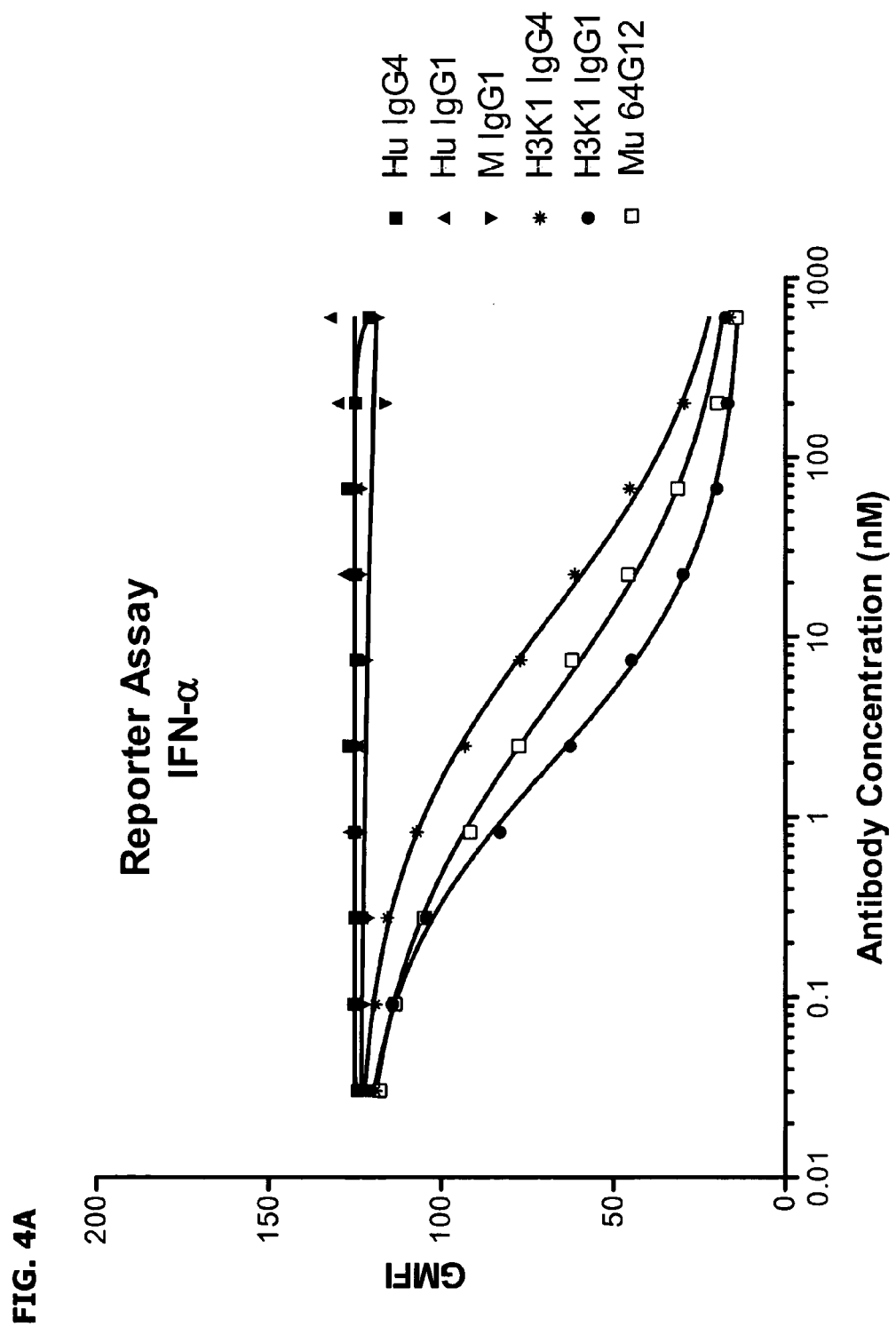

SEQUENCE LISTING

```
<160> NUMBER OF SEQ ID NOS: 49

<210> SEQ ID NO 1
<211> LENGTH: 7
<212> TYPE: PRT
<213> ORGANISM: Mus musculus

<400> SEQUENCE: 1

Thr Ser Gly Met Gly Ile Gly
1               5

<210> SEQ ID NO 2
<211> LENGTH: 16
<212> TYPE: PRT
<213> ORGANISM: Mus musculus

<400> SEQUENCE: 2

His Ile Trp Trp Asp Asp Asp Lys Tyr Tyr Asn Pro Ser Leu Lys Ser
1               5                   10                  15

<210> SEQ ID NO 3
<211> LENGTH: 11
<212> TYPE: PRT
<213> ORGANISM: Mus musculus

<400> SEQUENCE: 3

Asn Tyr Tyr Pro Tyr Asp Ala Trp Phe Asp Tyr
1               5                   10

<210> SEQ ID NO 4
<211> LENGTH: 12
<212> TYPE: PRT
<213> ORGANISM: Mus musculus

<400> SEQUENCE: 4

Ser Ala Ser Ser Ser Ile Asn Ser Asn His Leu His
1               5                   10

<210> SEQ ID NO 5
<211> LENGTH: 7
<212> TYPE: PRT
<213> ORGANISM: Mus musculus
```

```
<400> SEQUENCE: 5

Arg Thr Ser Ile Leu Ala Ser
1               5

<210> SEQ ID NO 6
<211> LENGTH: 9
<212> TYPE: PRT
<213> ORGANISM: Mus musculus

<400> SEQUENCE: 6

Gln Gln Gly Ser Asn Ile Pro Phe Thr
1               5

<210> SEQ ID NO 7
<211> LENGTH: 120
<212> TYPE: PRT
<213> ORGANISM: Mus musculus

<400> SEQUENCE: 7

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Ile Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Gln Leu Thr Ile Ser Arg Asp Thr Ser Thr Asn Gln Val
65                  70                  75                  80

Phe Leu Asn Ile Thr Ser Val Asp Thr Val Asp Ala Thr Tyr Tyr
                85                  90                  95

Cys Gly Arg Asn Tyr Tyr Pro Tyr Asp Ala Trp Phe Asp Tyr Trp Gly
                100                 105                 110

Gln Gly Thr Leu Val Thr Val Ser
        115                 120

<210> SEQ ID NO 8
<211> LENGTH: 120
<212> TYPE: PRT
<213> ORGANISM: Artificial
<220> FEATURE:
<223> OTHER INFORMATION: Synthetic

<400> SEQUENCE: 8

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Ile Gly Trp Ile Arg Gln Pro Pro Gly Lys Ala Leu Glu
        35                  40                  45

Trp Leu Ala His Ile Trp Trp Asp Asp Lys Tyr Tyr Asn Pro Ser
    50                  55                  60

Leu Lys Ser Arg Leu Thr Ile Ser Arg Asp Thr Ser Lys Asn Gln Val
65                  70                  75                  80

Val Leu Thr Met Thr Asn Met Asp Pro Val Asp Ala Thr Tyr Tyr
                85                  90                  95

Cys Gly Arg Asn Tyr Tyr Pro Tyr Asp Ala Trp Phe Asp Tyr Trp Gly
                100                 105                 110
```

Gln Gly Thr Leu Val Thr Val Ser
        115                 120

<210> SEQ ID NO 9
<211> LENGTH: 120
<212> TYPE: PRT
<213> ORGANISM: Artificial
<220> FEATURE:
<223> OTHER INFORMATION: Synthetic

<400> SEQUENCE: 9

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Arg Val Ser Trp Ile Arg Gln Pro Pro Gly Lys Ala Leu Glu
        35                  40                  45

Trp Leu Ala Arg Ile Asp Trp Asp Asp Lys Phe Tyr Ser Thr Ser
    50                  55                  60

Leu Lys Thr Arg Leu Thr Ile Ser Arg Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Gly Arg Asn Tyr Tyr Pro Tyr Asp Ala Trp Phe Asp Tyr Trp Gly
            100                 105                 110

Gln Gly Thr Leu Val Thr Val Ser
        115                 120

<210> SEQ ID NO 10
<211> LENGTH: 120
<212> TYPE: PRT
<213> ORGANISM: Artificial
<220> FEATURE:
<223> OTHER INFORMATION: Synthetic

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Phe Ser Gly Phe Thr Leu Ser Thr Ser
            20                  25                  30

Gly Met Gly Ile Gly Trp Val Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Arg Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Asn Tyr Tyr Pro Tyr Asp Ala Trp Phe Asp Tyr Trp Gly
            100                 105                 110

Gln Gly Thr Leu Val Thr Val Ser
        115                 120

<210> SEQ ID NO 11
<211> LENGTH: 120
<212> TYPE: PRT
<213> ORGANISM: Artificial
<220> FEATURE:
<223> OTHER INFORMATION: Synthetic

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Phe Ser Gly Phe Thr Leu Ser Thr Ser
            20                  25                  30

Gly Met Gly Ile Gly Trp Val Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Arg Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Asn Tyr Tyr Pro Tyr Asp Ala Trp Phe Asp Tyr Trp Gly
            100                 105                 110

Gln Gly Thr Leu Val Thr Val Ser
        115                 120

<210> SEQ ID NO 12
<211> LENGTH: 120
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (103)..(103)
<223> OTHER INFORMATION: The Xaa at position 103 can be Leu, Asn, Glu,
      Val, Ala, Cys, Gly, Ser, Arg, Asp, Met, His, Thr, Trp, Lys, or Ile

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Phe Ser Gly Phe Thr Leu Ser Thr Ser
            20                  25                  30

Gly Met Gly Ile Gly Trp Val Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Arg Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Asn Tyr Tyr Xaa Tyr Asp Ala Trp Phe Asp Tyr Trp Gly
            100                 105                 110

Gln Gly Thr Leu Val Thr Val Ser
        115                 120

<210> SEQ ID NO 13
<211> LENGTH: 120
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (110)..(110)
<223> OTHER INFORMATION: The Xaa at position 110 can be Leu, Glu, Gln,
      Arg, Val, Ala, Phe, Gly, Cys, Thr, Trp, His, Lys, Asp, Ser, or Ile

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Phe Ser Gly Phe Thr Leu Ser Thr Ser
            20                  25                  30

Gly Met Gly Ile Gly Trp Val Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Arg Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Asn Tyr Tyr Pro Tyr Asp Ala Trp Phe Asp Xaa Trp Gly
            100                 105                 110

Gln Gly Thr Leu Val Thr Val Ser
        115                 120

<210> SEQ ID NO 14
<211> LENGTH: 120
<212> TYPE: PRT
<213> ORGANISM: Artificial
<220> FEATURE:
<223> OTHER INFORMATION: Synthetic

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Phe Ser Gly Phe Thr Leu Ser Thr Ser
            20                  25                  30

Gly Ala Gly Ile Gly Trp Val Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Arg Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Asn Tyr Tyr Pro Tyr Asp Ala Trp Phe Asp Tyr Trp Gly
            100                 105                 110

Gln Gly Thr Leu Val Thr Val Ser
        115                 120

<210> SEQ ID NO 15
<211> LENGTH: 120
<212> TYPE: PRT
<213> ORGANISM: Artificial
<220> FEATURE:
<223> OTHER INFORMATION: Synthetic

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Phe Ser Gly Phe Thr Leu Ser Thr Ser
            20                  25                  30

Gly Met Gly Ile Gly Trp Val Arg Gln Ala Pro Gly Lys Gly Leu Glu
        35                  40                  45

-continued

```
Trp Val Ala His Ile Trp Trp Asp Asp Asp Lys Tyr Tyr Asn Pro Ser
         50                  55                  60
Leu Lys Ala Arg Phe Thr Ile Ser Arg Asp Thr Ser Lys Asn Thr Val
 65                  70                  75                  80
Tyr Leu Gln Met Asn Ser Leu Arg Ala Glu Asp Thr Ala Val Tyr Tyr
                 85                  90                  95
Cys Ala Arg Asn Tyr Tyr Pro Tyr Asp Ala Trp Phe Asp Tyr Trp Gly
                100                 105                 110
Gln Gly Thr Leu Val Thr Val Ser
            115                 120
```

<210> SEQ ID NO 16
<211> LENGTH: 120
<212> TYPE: PRT
<213> ORGANISM: Artificial
<220> FEATURE:
<223> OTHER INFORMATION: Synthetic

<400> SEQUENCE: 16

```
Glu Val Gln Leu Leu Glu Ser Gly Gly Gly Leu Val Gln Pro Gly Gly
  1               5                  10                  15
Ser Leu Arg Leu Ser Cys Ala Phe Ser Gly Phe Thr Leu Ser Thr Ser
                 20                  25                  30
Gly Ala Gly Ile Gly Trp Val Arg Gln Ala Pro Gly Lys Gly Leu Glu
             35                  40                  45
Trp Val Ala His Ile Trp Trp Asp Asp Asp Lys Tyr Tyr Asn Pro Ser
         50                  55                  60
Leu Lys Ala Arg Phe Thr Ile Ser Arg Asp Thr Ser Lys Asn Thr Val
 65                  70                  75                  80
Tyr Leu Gln Met Asn Ser Leu Arg Ala Glu Asp Thr Ala Val Tyr Tyr
                 85                  90                  95
Cys Ala Arg Asn Tyr Tyr Pro Tyr Asp Ala Trp Phe Asp Tyr Trp Gly
                100                 105                 110
Gln Gly Thr Leu Val Thr Val Ser
            115                 120
```

<210> SEQ ID NO 17
<211> LENGTH: 120
<212> TYPE: PRT
<213> ORGANISM: Artificial
<220> FEATURE:
<223> OTHER INFORMATION: Synthetic

<400> SEQUENCE: 17

```
Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Met Ser Thr Ser
                 20                  25                  30
Gly Met Gly Ile Gly Trp Ile Arg Gln Thr Pro Gly Lys Gly Leu Glu
             35                  40                  45
Trp Val Ala His Ile Trp Trp Asp Asp Asp Lys Tyr Tyr Asn Pro Ser
         50                  55                  60
Leu Lys Ser Arg Phe Thr Ile Ser Lys Asp Thr Ser Lys Asn Thr Leu
 65                  70                  75                  80
Tyr Leu Gln Met Asn Ser Leu Arg Ala Glu Asp Thr Ala Val Tyr Tyr
                 85                  90                  95
Cys Ala Arg Asn Tyr Tyr Pro Tyr Asp Ala Trp Phe Asp Tyr Trp Gly
                100                 105                 110
```

```
Gln Gly Thr Leu Val Thr Val Ser
        115                 120

<210> SEQ ID NO 18
<211> LENGTH: 120
<212> TYPE: PRT
<213> ORGANISM: Artificial
<220> FEATURE:
<223> OTHER INFORMATION: Synthetic

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Met Ser Thr Ser
            20                  25                  30

Gly Met Gly Ile Gly Trp Ile Arg Gln Thr Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ala Arg Phe Thr Ile Ser Arg Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asn Tyr Tyr Pro Tyr Asp Ala Trp Phe Asp Tyr Trp Gly
            100                 105                 110

Gln Gly Thr Leu Val Thr Val Ser
        115                 120

<210> SEQ ID NO 19
<211> LENGTH: 109
<212> TYPE: PRT
<213> ORGANISM: Mus musculus

<400> SEQUENCE: 19

Glu Ile Val Leu Thr Gln Ser Pro Thr Thr Met Ala Ala Ser Pro Gly
1               5                   10                  15

Glu Lys Ile Thr Ile Thr Cys Ser Ala Ser Ser Ser Ile Asn Ser Asn
            20                  25                  30

His Leu His Trp Tyr Gln Gln Lys Pro Gly Phe Ser Pro Lys Val Leu
        35                  40                  45

Ile Tyr Arg Thr Ser Ile Leu Ala Ser Gly Val Pro Thr Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Asn Ile Pro
                85                  90                  95

Phe Thr Phe Gly Ser Gly Thr Glu Leu Glu Ile Lys Arg
            100                 105

<210> SEQ ID NO 20
<211> LENGTH: 109
<212> TYPE: PRT
<213> ORGANISM: Artificial
<220> FEATURE:
<223> OTHER INFORMATION: Synthetic

<400> SEQUENCE: 20

Glu Ile Val Leu Thr Gln Ser Pro Asp Phe Gln Ser Val Thr Pro Lys
```

```
                1               5                   10                  15
Glu Lys Val Thr Ile Thr Cys Ser Ala Ser Ser Ser Ile Asn Ser Asn
                20                  25                  30

His Leu His Trp Tyr Gln Gln Lys Pro Gly Gln Ser Pro Lys Leu Leu
                35                  40                  45

Ile Tyr Arg Thr Ser Ile Leu Ala Ser Gly Val Pro Ser Arg Phe Ser
                50                  55                  60

Gly Ser Gly Ser Gly Thr Ser Phe Thr Leu Thr Ile Asn Ser Leu Glu
65                      70                  75                  80

Ala Glu Asp Val Ala Thr Tyr Tyr Cys Gln Gln Gly Ser Asn Ile Pro
                85                  90                  95

Phe Thr Phe Gly Gln Gly Thr Lys Leu Glu Ile Lys Arg
                100                 105

<210> SEQ ID NO 21
<211> LENGTH: 109
<212> TYPE: PRT
<213> ORGANISM: Artificial
<220> FEATURE:
<223> OTHER INFORMATION: Synthetic

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Ile Asn Ser Asn
                20                  25                  30

His Leu His Trp Tyr Gln Gln Lys Pro Gly Lys Ala Pro Lys Leu Leu
                35                  40                  45

Ile Tyr Arg Thr Ser Ile Leu Ala Ser Gly Val Pro Ser Arg Phe Ser
                50                  55                  60

Gly Ser Gly Ser Gly Thr Ser Phe Thr Leu Thr Ile Ser Ser Leu Gln
65                      70                  75                  80

Pro Glu Asp Phe Ala Thr Tyr Tyr Cys Gln Gln Gly Ser Asn Ile Pro
                85                  90                  95

Phe Thr Phe Gly Gln Gly Thr Lys Val Glu Ile Lys Arg
                100                 105

<210> SEQ ID NO 22
<211> LENGTH: 109
<212> TYPE: PRT
<213> ORGANISM: Artificial
<220> FEATURE:
<223> OTHER INFORMATION: Synthetic

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Ser Ala Ser Thr Ser Ile Asn Ser Asn
                20                  25                  30

His Leu His Trp Tyr Gln Gln Lys Pro Gly Lys Ala Pro Lys Leu Leu
                35                  40                  45

Ile Tyr Arg Thr Ser Ile Leu Ala Ser Gly Val Pro Ser Arg Phe Ser
                50                  55                  60

Gly Ser Gly Ser Gly Thr Ser Phe Thr Leu Thr Ile Ser Ser Leu Gln
65                      70                  75                  80

Pro Glu Asp Phe Ala Thr Tyr Tyr Cys Gln Gln Gly Ser Asn Ile Pro
                85                  90                  95
```

```
Phe Thr Phe Gly Gln Gly Thr Lys Val Glu Ile Lys Arg
            100                 105
```

<210> SEQ ID NO 23
<211> LENGTH: 109
<212> TYPE: PRT
<213> ORGANISM: Homo sapiens

<400> SEQUENCE: 23

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Ile Asn Ser Asn
            20                  25                  30

His Leu Asn Trp Tyr Gln Gln Lys Pro Gly Lys Ala Pro Lys Leu Leu
        35                  40                  45

Ile Tyr Arg Thr Ser Ile Leu Ala Ser Gly Val Pro Ser Arg Phe Ser
    50                  55                  60

Gly Ser Gly Ser Gly Thr Ser Phe Thr Leu Thr Ile Ser Ser Leu Gln
65                  70                  75                  80

Pro Glu Asp Phe Ala Thr Tyr Tyr Cys Gln Gln Gly Ser Asn Ile Pro
                85                  90                  95

Phe Thr Phe Gly Gln Gly Thr Lys Val Glu Ile Lys Arg
            100                 105
```

<210> SEQ ID NO 24
<211> LENGTH: 109
<212> TYPE: PRT
<213> ORGANISM: Artificial
<220> FEATURE:
<223> OTHER INFORMATION: Synthetic

<400> SEQUENCE: 24

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Ile Asn Ser Asn
            20                  25                  30

His Leu His Trp Tyr Gln Gln Lys Pro Gly Lys Ala Pro Lys Leu Leu
        35                  40                  45

Ile Tyr Arg Thr Ser Ile Leu Ala Ser Gly Val Pro Ser Arg Phe Ser
    50                  55                  60

Gly Ser Gly Ser Gly Thr Ser Phe Thr Leu Thr Ile Ser Ser Leu Gln
65                  70                  75                  80

Pro Glu Asp Phe Ala Thr Tyr Tyr Cys Gln Gln Thr Ser Asn Ile Pro
                85                  90                  95

Phe Thr Phe Gly Gln Gly Thr Lys Val Glu Ile Lys Arg
            100                 105
```

<210> SEQ ID NO 25
<211> LENGTH: 109
<212> TYPE: PRT
<213> ORGANISM: Artificial
<220> FEATURE:
<223> OTHER INFORMATION: Synthetic

<400> SEQUENCE: 25

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Thr Ser Ile Asn Ser Asn
            20                  25                  30
```

His Leu Asn Trp Tyr Gln Gln Lys Pro Gly Lys Ala Pro Lys Leu Leu
            35                  40                  45

Ile Tyr Arg Thr Ser Ile Leu Ala Ser Gly Val Pro Ser Arg Phe Ser
        50                  55                  60

Gly Ser Gly Ser Gly Thr Ser Phe Thr Leu Thr Ile Ser Ser Leu Gln
65                  70                  75                  80

Pro Glu Asp Phe Ala Thr Tyr Tyr Cys Gln Gln Gly Ser Asn Ile Pro
                85                  90                  95

Phe Thr Phe Gly Gln Gly Thr Lys Val Glu Ile Lys Arg
            100                 105

<210> SEQ ID NO 26
<211> LENGTH: 109
<212> TYPE: PRT
<213> ORGANISM: Artificial
<220> FEATURE:
<223> OTHER INFORMATION: Synthetic

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Ser Ala Ser Thr Ser Ile Asn Ser Asn
            20                  25                  30

His Leu His Trp Tyr Gln Gln Lys Pro Gly Lys Ala Pro Lys Leu Leu
            35                  40                  45

Ile Tyr Arg Thr Ser Ile Leu Ala Ser Gly Val Pro Ser Arg Phe Ser
        50                  55                  60

Gly Ser Gly Ser Gly Thr Ser Phe Thr Leu Thr Ile Ser Ser Leu Gln
65                  70                  75                  80

Pro Glu Asp Phe Ala Thr Tyr Tyr Cys Gln Gln Thr Ser Asn Ile Pro
                85                  90                  95

Phe Thr Phe Gly Gln Gly Thr Lys Val Glu Ile Lys Arg
            100                 105

<210> SEQ ID NO 27
<211> LENGTH: 109
<212> TYPE: PRT
<213> ORGANISM: Artificial
<220> FEATURE:
<223> OTHER INFORMATION: Synthetic

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Ile Asn Ser Asn
            20                  25                  30

His Leu Asn Trp Tyr Gln Gln Lys Pro Gly Lys Ala Pro Lys Leu Leu
            35                  40                  45

Ile Tyr Arg Thr Ser Ile Leu Ala Ser Gly Val Pro Ser Arg Phe Ser
        50                  55                  60

Gly Ser Gly Ser Gly Thr Ser Phe Thr Leu Thr Ile Ser Ser Leu Gln
65                  70                  75                  80

Pro Glu Asp Phe Ala Thr Tyr Tyr Cys Gln Gln Thr Ser Asn Ile Pro
                85                  90                  95

Phe Thr Phe Gly Gln Gly Thr Lys Val Glu Ile Lys Arg
            100                 105

<210> SEQ ID NO 28

```
<211> LENGTH: 109
<212> TYPE: PRT
<213> ORGANISM: Artificial
<220> FEATURE:
<223> OTHER INFORMATION: Synthetic

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Ser Ala Ser Thr Ser Ile Asn Ser Asn
            20                  25                  30

His Leu Asn Trp Tyr Gln Gln Lys Pro Gly Lys Ala Pro Lys Leu Leu
        35                  40                  45

Ile Tyr Arg Thr Ser Ile Leu Ala Ser Gly Val Pro Ser Arg Phe Ser
    50                  55                  60

Gly Ser Gly Ser Gly Thr Ser Phe Thr Leu Thr Ile Ser Ser Leu Gln
65                  70                  75                  80

Pro Glu Asp Phe Ala Thr Tyr Tyr Cys Gln Gln Thr Ser Asn Ile Pro
                85                  90                  95

Phe Thr Phe Gly Gln Gly Thr Lys Val Glu Ile Lys Arg
            100                 105

<210> SEQ ID NO 29
<211> LENGTH: 114
<212> TYPE: PRT
<213> ORGANISM: Artificial
<220> FEATURE:
<223> OTHER INFORMATION: Synthetic

<400> SEQUENCE: 29

Asp Ile Gln Met Thr Gln Ser Pro Ser Ser Leu Ser Ala Ser Val Gly
1               5                   10                  15

Asp Arg Ala Thr Ile Thr Cys Ser Ala Ser Ser Ser Ile Asn Ser Asn
            20                  25                  30

His Leu His Trp Tyr Leu Gln Lys Pro Gly Lys Ala Pro Lys Ala Leu
        35                  40                  45

Ile Tyr Arg Thr Ser Ile Leu Ala Ser Gly Ile Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Thr Ala Thr Tyr Tyr Cys Gln Gln Gly Ser Asn Ile Pro
                85                  90                  95

Phe Thr Phe Gly Gln Gly Thr Lys Val Glu Ile Lys Arg Thr Val Ala
            100                 105                 110

Ala Pro

<210> SEQ ID NO 30
<211> LENGTH: 114
<212> TYPE: PRT
<213> ORGANISM: Artificial
<220> FEATURE:
<223> OTHER INFORMATION: Synthetic

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Ser Ala Ser Thr Ser Ile Asn Ser Asn
            20                  25                  30

His Leu His Trp Tyr Leu Gln Lys Pro Gly Lys Ala Pro Lys Ala Leu
```

```
                35                  40                  45
Ile Tyr Arg Thr Ser Ile Leu Ala Ser Gly Ile Pro Ser Arg Phe Ser
         50                  55                  60
Gly Ser Gly Ser Gly Thr Asp Phe Thr Leu Thr Ile Ser Ser Leu Gln
 65                  70                  75                  80
Pro Glu Asp Thr Ala Thr Tyr Tyr Cys Gln Gln Gly Ser Asn Ile Pro
                 85                  90                  95
Phe Thr Phe Gly Gln Gly Thr Lys Val Glu Ile Lys Arg Thr Val Ala
                100                 105                 110
Ala Pro

<210> SEQ ID NO 31
<211> LENGTH: 114
<212> TYPE: PRT
<213> ORGANISM: Artificial
<220> FEATURE:
<223> OTHER INFORMATION: Synthetic

<400> SEQUENCE: 31

Asp Ile Gln Met Thr Gln Ser Pro Ser Ser Leu Ser Ala Ser Val Gly
 1               5                  10                  15
Asp Arg Ala Thr Ile Thr Cys Ser Ala Ser Ser Ile Asn Ser Asn
                 20                  25                  30
His Leu His Trp Tyr Leu Gln Lys Pro Gly Lys Ala Pro Lys Ala Leu
             35                  40                  45
Ile Tyr Arg Thr Ser Ile Leu Ala Ser Gly Ile Pro Ser Arg Phe Ser
         50                  55                  60
Gly Ser Gly Ser Gly Thr Ser Phe Thr Leu Thr Ile Ser Ser Leu Gln
 65                  70                  75                  80
Pro Glu Asp Thr Ala Thr Tyr Tyr Cys Gln Gln Gly Ser Asn Ile Pro
                 85                  90                  95
Phe Thr Phe Gly Gln Gly Thr Lys Val Glu Ile Lys Arg Thr Val Ala
                100                 105                 110
Ala Pro

<210> SEQ ID NO 32
<211> LENGTH: 114
<212> TYPE: PRT
<213> ORGANISM: Artificial
<220> FEATURE:
<223> OTHER INFORMATION: Synthetic

<400> SEQUENCE: 32

Asp Ile Gln Met Thr Gln Ser Pro Ser Ser Leu Ser Ala Ser Val Gly
 1               5                  10                  15
Asp Arg Val Thr Ile Thr Cys Ser Ala Ser Thr Ser Ile Asn Ser Asn
                 20                  25                  30
His Leu His Trp Tyr Leu Gln Lys Pro Gly Lys Ala Pro Lys Ala Leu
             35                  40                  45
Ile Tyr Arg Thr Ser Ile Leu Ala Ser Gly Ile Pro Ser Arg Phe Ser
         50                  55                  60
Gly Ser Gly Ser Gly Thr Ser Phe Thr Leu Thr Ile Ser Ser Leu Gln
 65                  70                  75                  80
Pro Glu Asp Thr Ala Thr Tyr Tyr Cys Gln Gln Gly Ser Asn Ile Pro
                 85                  90                  95
Phe Thr Phe Gly Gln Gly Thr Lys Val Glu Ile Lys Arg Thr Val Ala
                100                 105                 110
```

```
<210> SEQ ID NO 33
<211> LENGTH: 114
<212> TYPE: PRT
<213> ORGANISM: Artificial
<220> FEATURE:
<223> OTHER INFORMATION: Synthetic

<400> SEQUENCE: 33
```

Asp Ile Gln Met Thr Gln Ser Pro Ser Ser Leu Ser Ala Ser Val Gly
 1               5                  10                  15

Asp Arg Val Thr Ile Thr Cys Ser Ala Ser Ser Ser Ile Asn Ser Asn
            20                  25                  30

His Leu His Trp Tyr Leu Gln Lys Pro Gly Lys Ala Pro Lys Ala Leu
        35                  40                  45

Ile Tyr Arg Thr Ser Ile Leu Ala Ser Gly Ile Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Thr Ala Thr Tyr Tyr Cys Gln Gln Gly Ser Asn Ile Pro
                85                  90                  95

Phe Thr Phe Gly Gln Gly Thr Lys Val Glu Ile Lys Arg Thr Val Ala
            100                 105                 110

Ala Pro

```
<210> SEQ ID NO 34
<211> LENGTH: 114
<212> TYPE: PRT
<213> ORGANISM: Artificial
<220> FEATURE:
<223> OTHER INFORMATION: Synthetic

<400> SEQUENCE: 34
```

Asp Ile Gln Met Thr Gln Ser Pro Ser Ser Leu Ser Ala Ser Val Gly
 1               5                  10                  15

Asp Arg Ala Thr Ile Thr Cys Ser Ala Ser Ser Ser Ile Asn Ser Asn
            20                  25                  30

His Leu His Trp Tyr Gln Gln Lys Pro Gly Lys Ala Pro Lys Ala Leu
        35                  40                  45

Ile Tyr Arg Thr Ser Ile Leu Ala Ser Gly Ile Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Thr Ala Thr Tyr Tyr Cys Gln Gln Gly Ser Asn Ile Pro
                85                  90                  95

Phe Thr Phe Gly Gln Gly Thr Lys Val Glu Ile Lys Arg Thr Val Ala
            100                 105                 110

Ala Pro

```
<210> SEQ ID NO 35
<211> LENGTH: 114
<212> TYPE: PRT
<213> ORGANISM: Artificial
<220> FEATURE:
<223> OTHER INFORMATION: Synthetic

<400> SEQUENCE: 35
```

```
Asp Ile Gln Met Thr Gln Ser Pro Ser Ser Leu Ser Ala Ser Val Gly
1               5                   10                  15

Asp Arg Ala Thr Ile Thr Cys Ser Ala Ser Ser Ser Ile Asn Ser Asn
            20                  25                  30

His Leu His Trp Tyr Leu Gln Lys Pro Gly Lys Ala Pro Lys Leu Leu
        35                  40                  45

Ile Tyr Arg Thr Ser Ile Leu Ala Ser Gly Ile Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Thr Ala Thr Tyr Tyr Cys Gln Gln Gly Ser Asn Ile Pro
                85                  90                  95

Phe Thr Phe Gly Gln Gly Thr Lys Val Glu Ile Lys Arg Thr Val Ala
            100                 105                 110

Ala Pro

<210> SEQ ID NO 36
<211> LENGTH: 114
<212> TYPE: PRT
<213> ORGANISM: Artificial
<220> FEATURE:
<223> OTHER INFORMATION: Synthetic

<400> SEQUENCE: 36

Asp Ile Gln Met Thr Gln Ser Pro Ser Ser Leu Ser Ala Ser Val Gly
1               5                   10                  15

Asp Arg Ala Thr Ile Thr Cys Ser Ala Ser Ser Ser Ile Asn Ser Asn
            20                  25                  30

His Leu His Trp Tyr Leu Gln Lys Pro Gly Lys Ala Pro Lys Ala Leu
        35                  40                  45

Ile Tyr Arg Thr Ser Ile Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Thr Ala Thr Tyr Tyr Cys Gln Gln Gly Ser Asn Ile Pro
                85                  90                  95

Phe Thr Phe Gly Gln Gly Thr Lys Val Glu Ile Lys Arg Thr Val Ala
            100                 105                 110

Ala Pro

<210> SEQ ID NO 37
<211> LENGTH: 114
<212> TYPE: PRT
<213> ORGANISM: Artificial
<220> FEATURE:
<223> OTHER INFORMATION: Synthetic

<400> SEQUENCE: 37

Asp Ile Gln Met Thr Gln Ser Pro Ser Ser Leu Ser Ala Ser Val Gly
1               5                   10                  15

Asp Arg Ala Thr Ile Thr Cys Ser Ala Ser Ser Ser Ile Asn Ser Asn
            20                  25                  30

His Leu His Trp Tyr Leu Gln Lys Pro Gly Lys Ala Pro Lys Ala Leu
        35                  40                  45

Ile Tyr Arg Thr Ser Ile Leu Ala Ser Gly Ile Pro Ser Arg Phe Ser
    50                  55                  60

Gly Ser Gly Ser Gly Thr Asp Phe Thr Leu Thr Ile Ser Ser Leu Gln
```

```
                65                  70                  75                  80
Pro Glu Asp Phe Ala Thr Tyr Tyr Cys Gln Gln Gly Ser Asn Ile Pro
                    85                  90                  95

Phe Thr Phe Gly Gln Gly Thr Lys Val Glu Ile Lys Arg Thr Val Ala
                100                 105                 110

Ala Pro

<210> SEQ ID NO 38
<211> LENGTH: 360
<212> TYPE: DNA
<213> ORGANISM: Homo sapiens

<400> SEQUENCE: 38
gaggtgcagc tgttggagtc tgggggaggc ttggtacagc ctgggggggtc cctgagactc      60 tcctgtgcat tctccggatt caccctgagc acttctggta tgggtatagg ctgggtccgc     120
caggctcccg ggaaggggct ggagtgggtc gcacacattt ggtgggatga tgataagtac     180
tataatccat ccctgaagag tcggttcacc atctccagag acacttccaa gaacacggta     240
tatctgcaaa tgaacagcct gagagccgag gacactgcag tatattactg tgcgagaaat     300
tactatcctt acgacgcctg gtttgactac tggggtcaag gtaccctagt caccgtctca     360

<210> SEQ ID NO 39
<211> LENGTH: 327
<212> TYPE: DNA
<213> ORGANISM: Artificial
<220> FEATURE:
<223> OTHER INFORMATION: Synthetic

<400> SEQUENCE: 39
gatatccaga tgacccagtc cccgagctcc ctgtccgcct ctgtgggcga tagggtcacc      60
atcacctgca gtgccagctc aagtataaat tccaatcact acactggta tcaacagaaa     120 ccaggaaagg cgccgaaact gctgatttac aggacatcca ttctggcttc tggagtccct     180
tctcgcttct ctggttccgg atctgggacg tctttcactc tgaccatcag ctccctgcag     240
ccggaagact cgcaacttta ttactgtcag cagggtagta atatcccatt cactttcgga     300
cagggtacca aggtggagat caaacgt                                          327

<210> SEQ ID NO 40
<211> LENGTH: 360
<212> TYPE: DNA
<213> ORGANISM: Homo sapiens

<400> SEQUENCE: 40
gaggtgcagc tgttggagtc tgggggaggc ttggtacagc ctgggggggtc cctgagactc      60 tcctgtgcag cctccggctt caccatgagc acttccggaa tgggtatagg ctggatccgc     120
cagacccccg ggaaggggct cgagtgggtc gcacacattt ggtgggatga tgataagtac     180
tataatccat ccctgaaggc tagattcacc atctccagag acacttccaa gaacacgctg     240
tatctgcaaa tgaacagcct gagagccgag gacactgcag tatattactg tgcgagaaat     300
tactatcctt acgacgcctg gtttgactac tggggtcaag gtaccctagt caccgtctca     360

<210> SEQ ID NO 41
<211> LENGTH: 327
<212> TYPE: DNA
<213> ORGANISM: Artificial
<220> FEATURE:
<223> OTHER INFORMATION: Synthetic
```

<400> SEQUENCE: 41

```
gatatccaga tgacccagtc cccgagctcc ctgtccgcct ctgtgggcga tagggtcacc    60
atcacctgca gtgccagcac aagtataaat tccaatcact acactggta tcaacagaaa   120
ccaggaaagg cgccgaaact gctgatttac aggacatcca ttctggcttc tggagtccct   180
tctcgcttct ctggttccgg atctgggacg tctttcactc tgaccatcag ctccctgcag   240
ccggaagact tcgcaactta ttactgtcag cagggtagta atatcccatt cactttcgga   300
cagggtacca aggtggagat caaacgt                                       327
```

<210> SEQ ID NO 42
<211> LENGTH: 12
<212> TYPE: PRT
<213> ORGANISM: Homo sapiens

<400> SEQUENCE: 42

```
Cys Asn Phe Ser Ser Leu Lys Leu Asn Val Tyr Glu
1               5                   10
```

<210> SEQ ID NO 43
<211> LENGTH: 27
<212> TYPE: DNA
<213> ORGANISM: Mus musculus

<400> SEQUENCE: 43

```
atgggcagac ttacattctc attcctg                                        27
```

<210> SEQ ID NO 44
<211> LENGTH: 20
<212> TYPE: DNA
<213> ORGANISM: Mus musculus

<400> SEQUENCE: 44

```
cagtggatag acagatgggg                                                20
```

<210> SEQ ID NO 45
<211> LENGTH: 20
<212> TYPE: DNA
<213> ORGANISM: Mus musculus

<400> SEQUENCE: 45

```
actggatggt gggaagatgg                                                20
```

<210> SEQ ID NO 46
<211> LENGTH: 32
<212> TYPE: DNA
<213> ORGANISM: Mus musculus

<400> SEQUENCE: 46

```
ctcacccagt ctccaaccac catggctgca tc                                  32
```

<210> SEQ ID NO 47
<211> LENGTH: 96
<212> TYPE: PRT
<213> ORGANISM: Homo sapiens

<400> SEQUENCE: 47

```
Gln Val Thr Leu Lys Glu Ser Gly Pro Val Leu Val Lys Pro Thr Glu
1               5                   10                  15
Thr Leu Thr Leu Thr Cys Thr Val Ser Gly Phe Ser Leu Ser Asn Ala
            20                  25                  30
```

```
Arg Met Gly Val Ser Trp Ile Arg Gln Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

<210> SEQ ID NO 48
<211> LENGTH: 98
<212> TYPE: PRT
<213> ORGANISM: Homo sapiens

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 49
<211> LENGTH: 95
<212> TYPE: PRT
<213> ORGANISM: Homo sapiens

<400> SEQUENCE: 49

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro
                85                  90                  95
```

HUMANIZED ANTIBODIES TO INTERFERON ALPHA RECEPTOR-1 (IFNAR-1)

CROSS-REFERENCE TO RELATED APPLICATION

This application claims the benefit of the filing date of U.S. Ser. No. 60/465,058, filed Apr. 23, 2003, the entire contents of which are incorporated herein by reference.

BACKGROUND OF THE INVENTION

Type I interferons (IFN) (IFN-α, IFN-β, IFN-ω, IFN-τ) are a family of structurally related cytokines having antiviral, antitumor and immunomodulatory effects (Hardy et al, Blood. 97:473, 2001; Cutrone and Langer, J. Biol. Chem. 276:17140, 2001). The human IFNα locus includes two subfamilies. The first subfamily consists of 14 non-allelic genes and 4 pseudogenes having at least 80% homology. The second subfamily, αII or omega (ω), contains 5 pseudogenes and 1 functional gene which exhibits 70% homology with the IFNα genes (Weissmann and Weber, Prog. Nucl. Acid Res. Mol. Biol., 33:251-300, 1986). The subtypes of IFNα have different specific activities but they possess the same biological spectrum (Streuli et al. PNAS-USA 78:2848, 1981) and have the same cellular receptor (Agnet M. et al. in "Interferon 5" Ed. I. Gresser p. 1-22, Academic Press, London 1983).

The interferon β (IFN β) is encoded by a single gene which has approximately 50% homology with the IFNα genes.

Gamma interferon, which is produced by activated lymphocytes, does not possess any homology with the alpha/beta interferons and it does not react with their receptor.

All human type I interferons bind to a cell surface receptor (IFN alpha receptor, IFNAR) consisting of two transmembrane proteins, IFNAR-1 and IFNAR-2. IFNAR-1 is essential for high affinity binding and differential specificity of the IFNAR complex (Cutrone, 2001, supra). While functional differences for each of the type I IFN subtypes have not been identified, it is thought that each may exhibit different interactions with the IFNAR receptor components leading to potentially diverse signaling outcomes (Cook et al. (1996) J. Biol. Chem., 271:13448). In particular, studies utilizing mutant forms of IFNAR-1 and IFNAR-2 suggested that alpha and beta interferons signal differently through the receptor by interacting differentially with respective chains (Lewerenz et al. (1998) J. Mol. Biol. 282:585).

Early functional studies of type I IFNs focused on innate defense against viral infections (Haller et al. (1981) J. Exp. Med. 154:199; Lindenmann et al. (1981) Methods Enzymol. 78:181). More recent studies, however, implicate type I IFNs as potent immunoregulatory cytokines in the adaptive immune response. Specifically, type I IFNs have been shown to facilitate differentiation of naïve T cells along the Th1 pathway (Brinkmann et al. (1993) J. Exp. Med. 178:1655), to enhance antibody production (Finkelman et al. (1991) J. Exp. Med. 174:1179) and to support the functional activity and survival of memory T cells (Santini, et al. (2000) J. Exp. Med. 191:1777; Tough et al. (1996) Science 272:1947).

Recent work by a number of groups suggests that IFN-α may enhance the maturation or activation of dendritic cells (DCs) (Santini, et al. (2000) J. Exp. Med., 191:1777; Luft et al. (1998) J. Immunol., 161:1947; Luft et al. (2002) Int. Immunol. 14:367; Radvanyi et al. (1999) Scand. J. Immunol. 50:499). Furthermore, increased expression of type I interferons has been described in numerous autoimmune diseases (Foulis et al. (1987) Lancet, 2:1423; Hooks et al. (1982) Arthritis Rheum 25:396; Hertzog et al. (1988) Clin. Immunol. Immunopathol. 48:192; Hopkins and Meager (1988) Clin. Exp. Immunol. 73:88; Arvin and Miller (1984) Arthritis Rheum. 27:582). The most studied examples of this are insulin-dependent diabetes mellitus (IDDM) (Foulis (1987) supra) and systemic lupus erythematosus (SLE) (Hooks (1982) supra), which are associated with elevated levels of IFN-α, and rheumatoid arthritis (RA) (Hertzog (1988), Hopkins and Meager (1988), Arvin and Miller (1984), supra) in which IFN-β may play a more significant role.

Moreover, administration of interferon α has been reported to exacerbate underlying disease in patients with psoriasis and multiple sclerosis and to induce an SLE like syndrome in patients without a previous history of autoimmune disease. Interferon α has also been shown to induce glomerulonephritis in normal mice and to accelerate the onset of the spontaneous autoimmune disease of NZB/W mice. Further, IFN-α therapy has been shown in some cases to lead to undesired side effects, including fever and neurological disorders. Hence, there are pathological situations in which inhibition of type I IFN activity may be beneficial to the patient and a need exists for agents effective in inhibiting type I IFN activity.

SUMMARY OF THE INVENTION

The present invention provides antagonists of the biological activities of the human type I IFN. These antagonists can be used for therapeutic (including prophylaxis) purposes, for example in situations where the production or expression of type I-IFN (IFN α/β/ω/τ) is associated with pathological symptoms. Such antagonists can also be used for the diagnosis of various diseases or for the study of the evolution of such diseases. The invention provides humanized antibodies directed against the IFNAR-1 receptor in which murine CDR sequences have been grafted directly into unmodified human framework sequences, resulting in high affinity, functional antibodies. Furthermore, the invention provides humanized antibodies comprising additional antibody modifications in order to decrease the antigenicity of the antibody itself. The invention also provides antibody fragments of the above.

In one embodiment, the invention provides a humanized antibody or humanized antibody fragment that specifically binds IFN alpha receptor-1, comprising:

a heavy chain variable region comprising the complementarity determining region amino acid sequences of SEQ ID NO:1, SEQ ID NO:2, or SEQ ID NO:3; and a light chain variable region comprising the complementarity determining region amino acid sequences of SEQ ID NO:4, SEQ ID NO:5, or SEQ ID NO:6; and variable domain framework regions from the heavy and light chains of a human antibody or human antibody consensus framework, wherein the variable domain framework regions are unaltered from the human antibody or human antibody consensus framework.

In another embodiment, the invention provides a humanized antibody or humanized antibody fragment that specifically binds IFN alpha receptor-1, having a heavy chain variable region comprising:

the amino acid sequence of CDR1 (SEQ ID NO:1), CDR2 (SEQ ID NO:2), and CDR3 (SEQ ID NO:3) of murine antibody 64G12, wherein at least one amino acid substitution has been made in the amino acid sequence of CDR3 (SEQ ID NO:3), and variable domain framework regions derived from a human antibody or a human antibody consensus framework.

Preferably, the humanized antibody or humanized antibody fragment retains at least 50% of the IFN alpha receptor-1 binding affinity of the murine antibody 64G12. In this embodiment, the variable domain framework regions may be unaltered from the human antibody or human antibody consensus framework, or may contain specific substitutions within the framework residues. In a preferred embodiment, the antibody or antibody fragment comprises an amino acid substitution at position 4 of CDR3. Preferably, this substitution is a substitution of proline to an amino acid selected from the group consisting of: L, N, E, V, A, C, G, S, I, R, D, M, H, T, W, and K, more preferably an amino acid selected from group consisting of: L, E, V, A, C, G, S, I, R, D, M, T, W, and K. In another preferred embodiment, the antibody or antibody fragment comprises an amino acid substitution at position 11 of CDR3. Preferably, this substitution is a substitution of tyrosine to an amino acid selected from the group consisting of: L, E, Q, R, V, A, F, G, C, I, T, W, H, K, D, and S, more preferably to an amino acid selected from the group consisting of: E, R, V, A, F, and H. In yet another preferred embodiment, the antibody or antibody fragment further comprises a light chain variable region comprising the amino acid sequence of CDR1 (SEQ ID NO:4), CDR2 (SEQ ID NO:5), and CDR3 (SEQ ID NO:6) of murine antibody 64G12.

In another embodiment, the invention provides a humanized antibody or humanized antibody fragment that specifically binds IFN alpha receptor-1, comprising:

a heavy chain variable region comprising the amino acid sequence of CDR1 (SEQ ID NO:1), CDR2 (SEQ ID NO:2), and CDR3 (SEQ ID NO:3) of murine antibody 64G12; and a light chain variable region comprising the amino acid sequence of CDR1 (SEQ ID NO:4), CDR2 (SEQ ID NO:5), and CDR3 (SEQ ID NO:6) of murine antibody 64G12; and wherein the humanized antibody or humanized antibody fragment comprises at least one amino acid substitution at an amino acid position selected from the group consisting of: 24H, 29H, 37H, 40H, 71H, 78H, 19L, 37L, 46L, 58L, 70L, and 83L, wherein the amino acid position of each group member is indicated utilizing the numbering system set forth in Kabat.

In preferred embodiments, the amino acid substitution is a substitution of alanine for phenylalanine at residue 24H utilizing the numbering system set forth in Kabat, a substitution of methionine for leucine at residue 29H utilizing the numbering system set forth in Kabat, a substitution of alanine for leucine at residue 29H utilizing the numbering system set forth in Kabat, a substitution of isoleucine for valine at residue 37H and a substitution of threonine for alanine at residue 40H utilizing the numbering system set forth in Kabat, a substitution of proline for alanine at residue 40H utilizing the numbering system set forth in Kabat, a substitution of lysine for arginine at residue 71H utilizing the numbering system set forth in Kabat, a substitution of leucine for valine at residue 78H utilizing the numbering system set forth in Kabat, a substitution of alanine for valine at residue 19L utilizing the numbering system set forth in Kabat, a substitution of leucine for glutamine at residue 37L utilizing the numbering system set forth in Kabat, a substitution of alanine for leucine at residue 46L utilizing the numbering system set forth in Kabat, a substitution of isoleucine for valine at residue 58L utilizing the numbering system set forth in Kabat, a substitution of aspartic acid for serine at residue 70L utilizing the numbering system set forth in Kabat, or a substitution of threonine for phenylalanine at residue 83L utilizing the numbering system set forth in Kabat.

Other preferred humanized antibodies or humanized antibody fragments of the invention are those that comprise a heavy chain variable region amino acid sequence selected from the group consisting of SEQ ID NO:8 of FIG. 11B (H2), SEQ ID NO:10 of FIG. 1D (H3), SEQ ID NO:11 of FIG. 1E (M3), SEQ ID NO:14 of FIG. 1H (M3-A), SEQ ID NO:15 of FIG. 1I (M3-B), SEQ ID NO:16 of FIG. 1J (M3-A/B), SEQ ID NO:17 of FIG. 1K (DI M3) and SEQ ID NO:18 of FIG. 1L (DI M3-B); and a light chain variable region amino acid sequence selected from the group consisting of SEQ ID NO:20 of FIG. 2B (K6), SEQ ID NO:21 of FIG. 2C (K1), SEQ ID NO:22 of FIG. 2D (K1-C), SEQ ID NO:23 of FIG. 2E (K1-D), SEQ ID NO:24 of FIG. 2F (K1-E), SEQ ID NO:25 of FIG. 2G (K1-C/D), SEQ ID NO:26 of FIG. 2H (K1-C/E), SEQ ID NO:27 of FIG. 2I (K1-D/E), SEQ ID NO:28 of FIG. 2J (K1-C/D/E), SEQ ID NO:29 of FIG. 2K (DI K1) and SEQ ID NO:30 of FIG. 2L (DI K1-C). Preferred pairings of heavy and light chain variable regions include: a variable heavy chain amino acid sequence having an amino acid sequence as set forth in SEQ ID NO:8 of FIG. 1B (H2), and a variable light chain amino acid sequence having an amino acid sequence as set forth in SEQ ID NO:20 of FIG. 2B (K6), a variable heavy chain amino acid sequence having an amino acid sequence as set forth in SEQ ID NO:8 of FIG. 1B (H2), and a variable light chain amino acid sequence having an amino acid sequence as set forth in SEQ ID NO:21 of FIG. 2C (K1), a variable heavy chain amino acid sequence having an amino acid sequence as set forth in SEQ ID NO:10 of FIG. 1D (H3), and a variable light chain amino acid sequence having an amino acid sequence as set forth in SEQ ID NO:20 of FIG. 2B (K6), a variable heavy chain amino acid sequence having an amino acid sequence as set forth in SEQ ID NO:10 of FIG. 1D (H3), and a variable light chain amino acid sequence having an amino acid sequence as set forth in SEQ ID NO:21 of FIG. 2C (K1), a variable heavy chain amino acid sequence having an amino acid sequence as set forth in SEQ ID NO:11 of FIG. 1E (M3), and a variable light chain amino acid sequence having an amino acid sequence as set forth in SEQ ID NO:21 of FIG. 2C (K1), a variable heavy chain amino acid sequence having an amino acid sequence as set forth in SEQ ID NO:17 of FIG. 1K (DI M3), and a variable light chain amino acid sequence having an amino acid sequence as set forth in SEQ ID NO:21 of FIG. 2C (K1), a variable heavy chain amino acid sequence having an amino acid sequence as set forth in SEQ ID NO:15 of FIG. 1I (M3-B), and a variable light chain amino acid sequence having an amino acid sequence as set forth in SEQ ID NO:21 of FIG. 2C (K1), a variable heavy chain amino acid sequence having an amino acid sequence as set forth in SEQ ID NO:18 of FIG. 1L (DI M3-B), and a variable light chain amino acid sequence having an amino acid sequence as set forth in SEQ ID NO:21 of FIG. 2C (K1), a variable heavy chain amino acid sequence having an amino acid sequence as set forth in SEQ ID NO:11 of FIG. 1E (M3), and a variable light chain amino acid sequence having an amino acid sequence as set forth in SEQ ID NO:22 of FIG. 2D (K1-C), a variable heavy chain amino acid sequence having an amino acid sequence as set forth in SEQ ID NO:15 of FIG. 1I (M3-B), and a variable light chain amino acid sequence having an amino acid sequence as set forth in SEQ ID NO:22 of FIG. 2D (K1-C), a variable heavy chain amino acid sequence having an amino acid sequence as set forth in SEQ ID NO:17 of FIG. 1K (DI M3), and a variable light chain amino acid sequence having an amino acid sequence as set forth in SEQ ID NO:22 of FIG. 2D (K1-C), or a variable heavy chain amino acid sequence having an amino acid sequence as set forth in SEQ ID NO:18 of FIG. 1L (DI M3-B), and a variable light chain amino acid sequence having an amino acid sequence as set forth in SEQ ID NO:22 of FIG. 2D (K1-C).

In other embodiments, the humanized antibodies of the invention further comprise human heavy and light constant domains. In a preferred embodiment, the human heavy constant region is selected from the group consisting of human gamma 1, gamma 2, gamma 3, and gamma 4. More preferably, the human heavy constant region is gamma 1. In yet other embodiments, the humanized antibodies of the invention has an IFN alpha receptor-1 binding affinity with a $K_D$ of $1\times10^{-7}$ M or less, more preferably a binding affinity with a $K_D$ of $1\times10^{-8}$ M or less. By a "a binding affinity with a $K_D$ of $1\times10^{-7}$ M or less" is meant a binding affinity of $1\times10^{-7}$ M or a greater overall binding affinity. In other embodiments, the binding affinity is within a range of $1\times10^{-7}$ to $5\times10^{-10}$ M, or within a range of $1\times10^{-8}$ to $5\times10^{-10}$ M, or within a range of $1\times10^{-9}$ to $5\times10^{-10}$ M. In still other embodiments, the humanized anti-IFNAR-1 antibodies, or antibody fragments, of the invention are biologically active in vitro and in vivo and inhibit biological responses induced by multiple type I interferons.

Another aspect of the invention pertains to methods for inhibiting the binding of type-I interferon to IFN alpha receptor-1 on a cell expressing IFN alpha receptor-1. The method comprises contacting the cell with a humanized antibody or humanized antibody fragment of the invention such that the binding of the type 1 interferon to IFN alpha receptor-1 is inhibited. In yet another aspect, the invention pertains to methods for inhibition of an immune response in a subject. The method comprises administering to the subject a humanized antibody or humanized antibody fragment of the invention such that an immune response is inhibited. The immune response to be inhibited can be one in which, for example, the expression of MHC class I or MHC class II on cells is modulated, or in which dendritic cell development is induced or which is characterized by a mixed lymphocyte reaction. Inhibition of the immune response can include inhibition of allostimulatory cells, such as GMCSF/IFN induced dendritic cells.

The invention provides further methods for treating autoimmune disorders, transplant rejection, or Graft Versus Host Disease (GVHD) in a subject. The methods comprise administering to the subject a humanized antibody or antibody fragment of the invention such that the subject is treated for the autoimmune disorder, transplant rejection, or GVHD. In one embodiment, the autoimmune disorder is Inflammatory Bowel Disease (IBD). In another embodiment, the autoimmune disorder is Systemic Lupus Erythematosus (SLE). In yet another embodiment, the autoimmune disorder is Insulin Dependent Diabetes Mellitus (IDDM). In yet another embodiment, the autoimmune disorder is rheumatoid arthritis (RA).

The invention still further provides methods to modify serum C reactive protein (CRP) levels in a subject, methods to modify serum neopterin levels in a subject, and methods to modify B-cell proliferation in a subject, which methods comprise administering a humanized antibody or antibody fragment of the invention to the subject.

In another aspect, the invention also provides chimeric anti-IFNAR-1 antibodies, or antibody fragments. Preferably, the chimeric antibody comprises a heavy chain variable domain and a light chain variable domain of a murine anti-IFNAR-1 antibody 64G12 (SEQ ID NO:7 of FIG. 1A and SEQ ID NO:19 of FIG. 2A, respectively), operably linked to human heavy and light chain constant regions. Preferred human heavy chain constant regions include human gamma 1, human gamma 2, human gamma 3 and human gamma 4, more preferably human gamma 1.

BRIEF DESCRIPTION OF THE DRAWINGS

FIGS. 1A-1L are schematics showing amino acid sequences of a murine heavy chain variable region and of the heavy chain variable regions of anti-IFNAR-1 antibodies of the invention. The CDR1, CDR2 and CDR3 regions are underlined. Substitutions made at CDR or framework residues are italicized.

FIG. 1A is the original murine 64G12 heavy chain variable region. It was cloned by amplifying from a cDNA library synthesized from mRNA extracted from the 64G12 hybridoma combining a 5' primer (atgggcagacttacattctcattcctg) (SEQ ID NO:43), and a 3' primer (cagtggatagacagatggggg) (SEQ ID NO:44) that is complimentary to the murine IgG1 CH1 domain. CDR sequences of the 64G12 heavy chain are underlined.

FIG. 1B is a heavy chain variable region designed by combining the CDRs and other amino acids from the murine sequence with the human immunoglobin heavy chain germline DP-28 framework sequence.

FIG. 1C is a heavy chain variable region designed by combining CDR-3 from the murine sequence with the human immunoglobin heavy chain germline DP-28 framework sequence.

FIG. 1D is a heavy chain variable region designed by combining the CDR's and other amino acids from the murine sequence with a human immunoglobin heavy chain framework sequence.

FIG. 1E is a heavy chain variable region designed by combining the CDR's and other amino acids from the murine sequence with the human immunoglobin heavy chain germline DP-47 framework sequence.

FIG. 1F is a heavy chain M3 with the amino acid X substituted with L, N, E, V, A, C, G, S, R, D, M, H, T, W, K, or I.

FIG. 1G is heavy chain M3 with the amino acid X substituted with L, E, Q, R, V, A, F, G, C, T, W, H, K, D, S, or I.

FIG. 1H is heavy chain M3 with a T-cell epitope removed by substituting an amino acid in the CDR-1 region (italicized).

FIG. 1I is heavy chain M3 with a T-cell epitope removed by substituting an amino acid in the CDR-2 region (italicized).

FIG. 1J is heavy chain M3 with two T-cell epitopes removed by substituting amino acids in the CDR-1 and 2 regions (italicized).

FIG. 1K is heavy chain M3 with all of its potential T-cell epitopes removed by changing the italicized amino acids in the framework region.

FIG. 1L is heavy chain M3 with all of its potential T-cell epitopes removed by changing the italicized amino acids in the framework and CDR-2 region.

FIGS. 2A-2S are schematics showing the amino acid sequences of a murine light chain variable region and of the light chain variable regions of anti-IFNAR-1 antibodies of the invention. The CDR1, CDR2 and CDR3 regions are underlined. Substitutions made at CDR or framework residues are italicized.

FIG. 2A is the original murine 64G12 light chain variable region. It was cloned by amplifying from a cDNA library synthesized from mRNA extracted from the 64G12 hybridoma combining a 5' primer (ctcacccagtctccaaccaccatggctgcatc) (SEQ ID NO:46) that is based upon the N-terminal peptide sequence of the antibody and a 3' primer (actggatggtgggaagatgg) (SEQ ID NO:45) that is complementary to the murine kappa constant domain. CDR sequences of the 64G12 light chain are underlined.

FIG. 2B is a light chain variable region designed by combining the CDRs and other amino acids from the murine sequence with the human immunoglobin light chain germline DPk-26 framework sequence.

FIG. 2C is a light chain variable region designed by combining the CDRs and other amino acids from the murine sequence with a human immunoglobin kappa chain framework sequence.

FIG. 2D is light chain K1 with one of its potential T-cell epitopes removed by changing the italicized amino acid in CDR-1.

FIG. 2E is light chain K1 with one of its potential T-cell epitopes removed by changing the italicized amino acid in CDR-1.

FIG. 2F is light chain K1 with one of its potential T-cell epitopes removed by changing the italicized amino acid in CDR-3.

FIG. 2G is light chain K1 with two of its potential T-cell epitopes removed by changing the italicized amino acids in CDR-1.

FIG. 2H is light chain K1 with two of its potential T-cell epitopes removed by changing the italicized amino acids in CDR-1 and 3.

FIG. 2I is light chain K1 with two of its potential T-cell epitopes removed by changing the italicized amino acids in CDR-1 and 3.

FIG. 2J is light chain K1 with three of its potential T-cell epitopes removed by changing the italicized amino acids in CDR-1 and 3.

FIG. 2K is light chain K1 with all of its potential T-cell epitopes removed by changing the italicized amino acids in the framework region.

FIG. 2L is light chain K1 with all of its potential T-cell epitopes removed by changing the italicized amino acids in the framework region and CDR-1.

FIG. 2M is light chain K1 with five of the six potential T-cell epitopes removed by changing the italicized amino acids in the framework region.

FIG. 2N is light chain K1 with five of the six potential T-cell epitopes removed by changing the italicized amino acids in the framework region and CDR-1.

FIG. 2O is light chain K1 with five of the six potential T-cell epitopes removed by changing the italicized amino acids in the framework region.

FIG. 2P is light chain K1 with five of the six potential T-cell epitopes removed by changing the italicized amino acids in the framework region.

FIG. 2Q is light chain K1 with five of the six potential T-cell epitopes removed by changing the italicized amino acids in the framework region.

FIG. 2R is light chain K1 with five of the six potential T-cell epitopes removed by changing the italicized amino acids in the framework region.

FIG. 2S is light chain K1 with five of the six potential T-cell epitopes removed by changing the italicized amino acids in the framework region.

FIGS. 3A-3D show the nucleic acid sequences of the heavy chain variable regions M3 (FIG. 3A) and DI M3-B (FIG. 3C), and the light chain variable regions K1 (FIG. 3B) and K1-C (FIG. 3D).

FIGS. 4A-4B are graphs showing the inhibition of IFN-α (FIG. 4A) and IFN-β (FIG. 4B) activity by anti-IFNAR-1 humanized antibodies as measured in an interferon-responsive reporter gene assay.

Figure 4B:
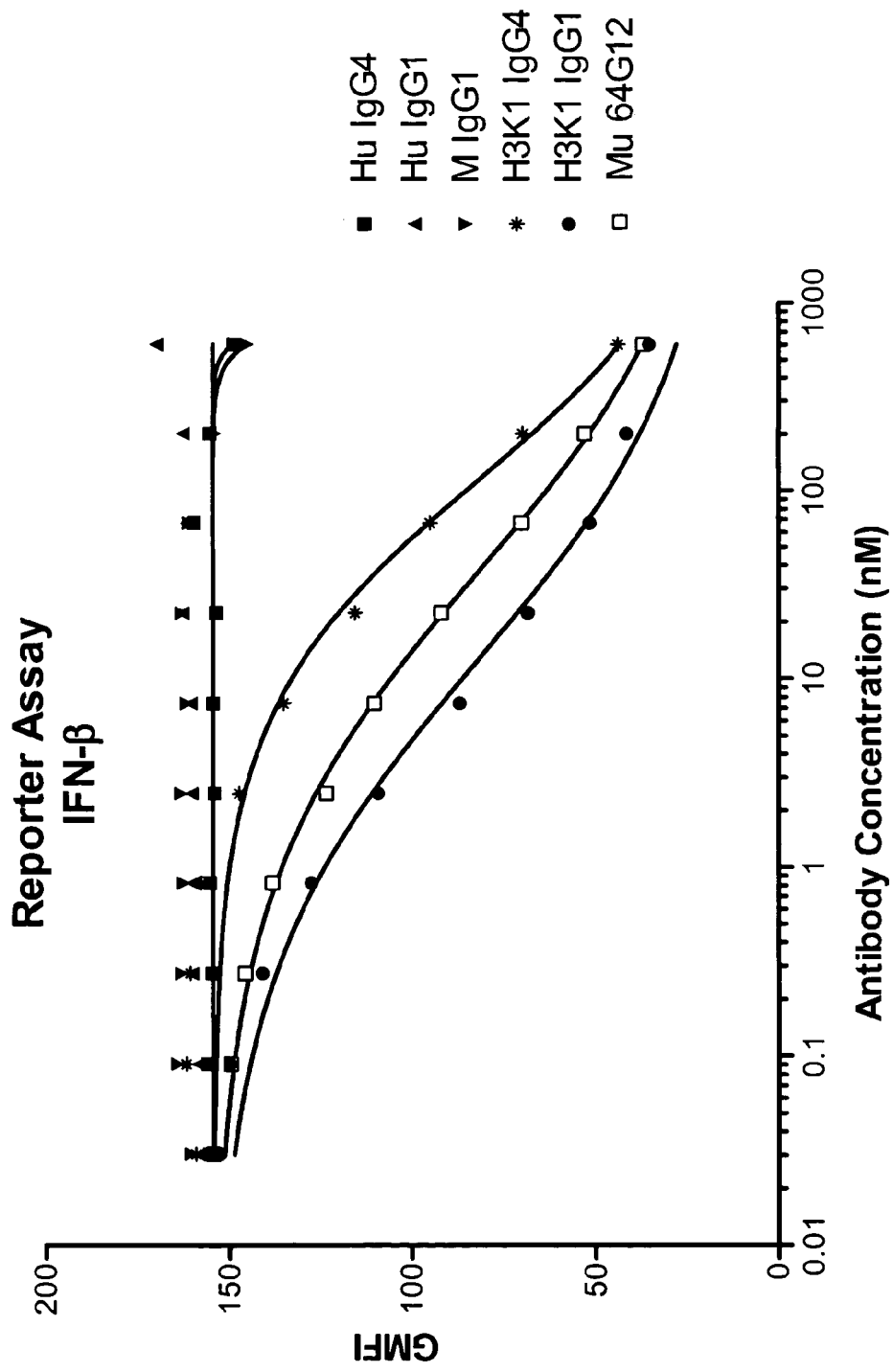

DETAILED DESCRIPTION OF THE INVENTION

The present invention provides novel humanized and chimeric antibodies directed against the Interferon-alpha receptor 1 (IFNAR-1). In one aspect, the humanized antibodies of the present invention contain framework (FR) regions that are unaltered from human germline sequences. In other aspects, the humanized antibodies contain mutations within CDR regions, as compared to the donor murine antibody, preferably in CDR3, for example to improve the binding of the antibody. In yet other aspects, the humanized antibodies contain mutations within the framework regions, as compared to the human germline sequences, for example to reduce the immunogenicity of the antibodies (e.g., to remove T cell epitopes). The antibodies of the invention can be used for therapeutic purposes, for example in cases where production or expression of type I interferon (IFN) is associated with pathological symptoms.

It has been discovered that the CDRs of the murine anti-human IFNAR-1 monoclonal antibody 64G12 can be grafted onto the FRs of a human antibody sequence to provide humanized antibodies and antibody-derived reagents that have the antigen binding properties of the 64G12 anti-IFNAR-1 mAb and a high antigen binding affinity, while also exhibiting reduced induction of HAMA and augmented effector activities. Preferably, the human framework amino acid sequences are selected such that the resulting antibody is likely to be suitable for in vivo administration in humans. This can be determined, e.g., based on previous usage of antibodies containing such human FRs. Preferably, the human FRs will not themselves be significantly immunogenic.

In one embodiment, the present invention is directed to humanized antibodies which specifically bind IFNAR-1 and are able to block the action of type I interferons. Preferably, such humanized antibodies will be derived from antibodies having good binding affinity to IFNAR-1 and good blocking activity toward all type I interferons, such as 64G12. Preferably, such humanized antibodies will be derived from 64G12, a murine antibody of the IgG isotype, which has been reported to bind to IFNAR-1 with high affinity ($K_D=1.2\times10^{-9}$ M).

Preferably, the humanized antibodies of the present invention will bind the same epitope as 64G12. Such antibodies can be identified based on their ability to compete with 64G12 for binding to IFNAR-1 or to IFNAR-1-expressing cells. The epitope for which 64G12 binds has been found to include the peptide: CNFSSLKLNVYE (SEQ ID NO:42). This peptide is in the sub domain 1 of the extracellular portion of IFNAR1. Specific substitutions within this peptide significantly inhibit antibody binding, and also inhibit binding and activity of type-I IFNs.

The murine anti-IFNAR-1 monoclonal antibody 64G12, and its production, have been described previously (U.S. Pat. No. 5,919,453) and has been deposited at the ECACC (European Collection of Animal Cell Cultures Porton Down Salisbury, Wiltshire SP4 056, United Kingdom) on Feb. 26, 1992.

As discussed above, humanized antibodies afford potential advantages over murine and also chimeric antibodies, e.g., reduced immunogenicity in humans. This is advantageous because it should reduce and potentially eliminate the eliciting of a HAMA response when such humanized antibodies are administered in vivo, e.g., for treatment of autoimmune diseases such as SLE, IDDM, RA, etc or for prevention of transplant rejection or GVHD. Also, such antibodies may exhibit improved, pharmacokinetic properties.

The humanized antibody of the present invention may comprise a complete antibody molecule, having full length heavy and light chains; a fragment thereof, such as a Fab, Fab', (Fab')$_2$, or Fv fragment; a single chain antibody fragment, e.g. a single chain Fv, a light chain or heavy chain monomer or dimer; multivalent monospecific antigen binding proteins comprising two, three, four or more antibodies or fragments thereof bound to each other by a connecting structure; or a fragment or analogue of any of these or any other molecule with the same specificity as MAb 64G12. In a preferred embodiment the antibody comprises a complete antibody molecule, having full length heavy and light chains.

In order that the present invention may be more readily understood, certain terms are first defined. Additional definitions are set forth throughout the detailed description.

The term "Interferon alpha receptor-1," "IFNAR-1," and "IFNAR-1 antigen" are used interchangeably herein, and include variants, isoforms and species homologs of human IFNAR-1. Accordingly, human antibodies of the invention may, in certain cases, cross-react with IFNAR-1 from species other than human, or other proteins which are structurally related to human IFNAR-1 (e.g., human IFNAR-1 homologs). In other cases, the antibodies may be completely specific for human IFNAR-1 and not exhibit species or other types of cross-reactivity.

The term "antibody" as referred to herein includes whole antibodies, including those of the IgG, IgM and IgA isotypes, and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The IgG heavy chain constant region is comprised of four domains, $C_{H1}$, hinge, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., IFNAR-1). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883) or via other means such as the use of disulphide bonds or through dimerization motifs. Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

An "isolated antibody," as used herein, is intended to refer to an antibody which is substantially free of other antibodies having different antigenic specificities (e.g., an isolated antibody that specifically binds to IFNAR-1 is substantially free of antibodies that specifically bind antigens other than IFNAR-1). An isolated antibody that specifically binds to an epitope, isoform or variant of human IFNAR-1 may, however, have cross-reactivity to other related antigens, e.g., from other species (e.g., IFNAR-1 species homologs). Moreover, an isolated antibody may be substantially free of other cellular material and/or chemicals. In one embodiment of the invention, a combination of "isolated" monoclonal antibodies having different specificities are combined in a well defined composition.

As used herein, "specific binding" refers to antibody binding to a predetermined antigen. Typically, the antibody binds with a dissociation constant ($K_D$) of $10^{-7}$ M or less, and binds to the predetermined antigen with a $K_D$ that is at least two-fold less than its $K_D$ for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

As used herein, the term "high affinity" for an IgG antibody refers to an antibody having a $K_D$ of $10^{-8}$ M or less, more preferably $10^{-9}$ M or less and even more preferably $10^{-10}$ M or less. However, "high affinity" binding can vary for other antibody isotypes. For example, "high affinity" binding for an IgM isotype refers to an antibody having a $K_D$ of $10^{-7}$ M or less, more preferably $10^{-8}$ M or less.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M).

As used herein, "isotype" refers to the antibody class (e.g., IgM, IgA or IgG1) that is encoded by heavy chain constant region genes.

As used herein, "isotype switching" refers to the phenomenon by which the class, or isotype, of an antibody changes from one Ig class to one of the other Ig classes.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "unrearranged" or "germline configuration" as used herein in reference to a V segment refers to the configuration wherein the V segment is not recombined so as to be immediately adjacent to a D or J segment.

The term "nucleic acid molecule", as used herein, is intended to include DNA molecules and RNA molecules. A nucleic acid molecule may be single-stranded or double-stranded, but preferably is double-stranded DNA.

As disclosed and claimed herein, the sequences set forth include "conservative sequence modifications", i.e., nucleotide and amino acid sequence modifications which do not significantly affect or alter the binding characteristics of the antibody encoded by the nucleotide sequence or containing the amino acid sequence. Such conservative sequence modifications include nucleotide and amino acid substitutions, additions and deletions. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-IFNAR-1 antibody is preferably replaced with another amino acid residue from the same side chain family.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available from Accelrys®), using a NWSgapdna.CMP matrix and a gap weight of 40, 50, 60, 70, or 80 and a length weight of 1, 2, 3, 4, 5, or 6. The percent identity between two nucleotide or amino acid sequences can also determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available from Accelrys®), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. See the National Center for Biotechnology website, ncbi.nlm.nih.gov).

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. *Current Protocols in Molecular Biology*, Greene Publishing and Wiley Interscience, New York (1987).

The nucleic acid compositions of the present invention, while often in a native sequence (except for modified restriction sites and the like), from either cDNA, genomic or mixtures may be mutated, thereof in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, CHO cells and lymphocytic cells.

As used herein, the term "subject" includes any human or nonhuman animal. The term "nonhuman animal" includes all vertebrates, e.g., mammals and non-mammals, such as nonhuman primates, sheep, dog, cow, chickens, amphibians, reptiles, etc.

Various aspects of the invention are described in further detail in the following subsections.

Production of Humanized Antibodies to IFNAR-1

The subject humanized antibodies are produced by obtaining nucleic acid sequences encoding the variable heavy ($V_H$) and variable light chains ($V_L$) of an antibody which binds IFNAR-1 (preferably 64G12), identifying the CDRs in said $V_H$ and $V_L$ sequences, and grafting such CDR-encoding nucleic acid sequences onto selected human framework-encoding nucleic acid sequences. Methods for cloning nucleic acid sequences encoding immunoglobulins are well known in the art. Such methods will generally involve the amplification of the immunoglobulin-encoding sequences to be cloned using appropriate primers by polymerase chain reaction (PCR). Primers suitable for amplifying immunoglobulin nucleic acid sequences, and specifically murine variable heavy and variable light sequences, have been reported in the literature. After such immunoglobulin-encoding sequences have been cloned, they will be sequenced by methods well known in the art. This will be effected in order to identify the $V_H$- and $V_L$-encoding sequences, and more specifically the portions thereof which encode the CDRs and FRs. This can be effected by well known methods which include, e.g., those disclosed in U.S. Pat. No. 4,816,397 to Boss et al. and U.S. Pat. No. 5,225,539 to Winter.

Once the DNA sequences encoding the CDRs and FRs of the antibody which is to be humanized have been identified, the amino acid sequences encoding the CDRs are then identified (deduced based on the nucleic acid sequences and the genetic code and by comparison to previous antibody sequences) and the CDR-encoding nucleic acid sequences are grafted onto selected human FR-encoding sequences. This may be accomplished by use of appropriate primers and linkers. Methods for selecting suitable primers and linkers to provide for ligation of desired nucleic acid sequences is well within the purview of the ordinary artisan.

As discussed above, the selected human FRs used for humanization will preferably be those that are likely to be suitable for in vivo administration, i.e. they are not in themselves immunogenic in humans.

After the CDR-encoding sequences are grafted onto the selected human FR-encoding sequences, the resultant DNA sequences encoding the "humanized" variable heavy and variable light sequences is then expressed to produce a humanized Fv or joined to human constant region sequences to produce humanized antibody which binds IFNAR-1. Typically, the humanized $V_H$ and $V_L$ sequences will be expressed as part of a whole αIFNAR-1 antibody molecule, i.e. as a fusion protein with human constant domain sequences whose encoding DNA sequences have been obtained from a commercially available library or which have been obtained using, e.g., one of the above-described methods for obtaining DNA sequences. The light or heavy chain variable domains of the humanized antibody molecule may be fused to human light or heavy chain constant domains as appropriate, (the term 'heavy chain constant domains' as used herein are to be understood to include hinge regions unless specified otherwise. The human constant domains of the humanized antibody molecule, where present, may be selected having regard to the proposed function of the antibody, in particular the lack of effector functions which may be required. For example, the heavy chain constant domains fused to the heavy chain variable region may be human IgA, IgG or IgM domains. Preferably human IgG domains are used. Light chain human constant domains which may be fused to the light chain variable region include human Lambda or human Kappa chains. Preferably human kappa chain domains are used.

Analogues of human constant domains may alternatively be advantageously used. These include those constant domains containing one or more additional amino acids than the corresponding human domain or those constant domains wherein one or more existing amino acids of the corresponding human domain has been deleted or altered. Such domains may be obtained, for example, by oligonucleotide directed mutagenesis. However, the $V_H$ and $V_L$ sequences can also be expressed in the absence of constant sequences to produce a humanized αIFNAR-1 Fv. Nevertheless, fusion of human constant sequences is potentially desirable because the resultant humanized αIFNAR-1 antibody may have a substantially improved pharmacokinetic profile. Methods for synthesizing DNA encoding a protein of known sequence are well known in the art. Using such methods, DNA sequences which encode the subject humanized $V_L$ and $V_H$ sequences (with or without constant regions) are synthesized, and then expressed in a vector system suitable for expression of recombinant antibodies. This may be effected in any vector system which provides for the subject humanized $V_L$ and $V_H$ sequences to be expressed as a fusion protein with human constant domain sequences and to associate to produce functional (antigen binding) antibodies or antibody fragments. Useful methods are set forth, e.g., in U.S. Pat. No. 4,816,397 to Boss et al. and U.S. Pat. No. 5,225,539 to Winter.

Expression vectors and host cells suitable for expression of recombinant antibodies and humanized antibodies in particular, are well known in the art. The following references are representative of methods and vectors suitable for expression of recombinant immunoglobulins which may be utilized in carrying out the present invention: Weidle et al., Gene, 51: 21-29 (1987); Dorai et al., J. Immunol., 13(12):4232-4241 (1987); De Waele et al., Eur. J. Biochem., 176:287-295 (1988); Colcher et al., Cancer Res., 49:1738-1745 (1989); Wood et al., J. Immunol., 145(9):3011-3016 (1990); Bulens et al., Eur. J. Biochem., 195:235-242 (1991); Beldsington et al., Biol. Technology, 10:169 (1992); King et al., Biochem. J., 281:317-323 (1992); Page et al., Biol. Technology, 9:64 (1991); King et al., Biochem. J., 290:723-729 (1993); Chaudhary et al., Nature, 339:394-397 (1989); Jones et al., Nature, 321:522-525 (1986); Morrison and Oi, Adv. Immunol., 44:65-92 (1989); Benhar et al., Proc. Natl. Acad. Sci. USA, 91:12051-12055 (1994); Singer et al., J. Immunol., 150:2844-2857 (1993); Couto et al., Hybridoma, 13(3):215-219 (1994); Queen et al., Proc. Natl. Acad. Sci. USA, 86:10029-10033 (1989); Caron et al., Cancer Res., 52:6761-6767 (1992); Coloura et al, J. Immunol. Meth., 152:89-109 (1992). Moreover, vectors suitable for expression of recombinant antibodies are commercially available. The vector may, e.g., be a bare nucleic acid segment, a carrier-associated nucleic acid segment, a nucleoprotein, a plasmid, a virus, a viroid, or a transposable element.

Host cells known to be capable of expressing functional immunoglobulins include, e.g.: mammalian cells such as Chinese Hamster Ovary (CHO) cells; COS cells; myeloma cells, such as NS0 and SP2/0 cells; bacteria such as *Escherichia coli*; yeast cells such as *Saccharomyces cerevisiae*; and other host cells. Of these, CHO cells are used by many researchers given their ability to effectively express and secrete immunoglobulins. NS0 cells are one of the preferred types of host cells useful in the present invention.

Essentially, recombinant expression of humanized antibodies is obtained by one of two general methods. In the first method, the host cells are transfected with a single vector which provides for the expression of both $V_H$ and $V_L$ variable sequences optionally fused to selected constant regions. In the second method, host cells are transfected with two vectors, each of which provides for expression of either the $V_H$ or $V_L$ sequence, each optionally fused to a selected constant region.

Human constant domain sequences are well known in the art, and have been reported in the literature. Preferred human constant light chain sequences ($C_L$) include the kappa and lambda constant light sequences. Preferred human constant heavy chain sequences include human gamma 1, human gamma 2, human gamma 3, human gamma 4, and mutated versions thereof which provide for altered effect or function, e.g., enhanced in vivo half-life, reduced Fc receptor binding, and the like.

After expression, the antigen binding affinity of the resultant humanized antibody will be assayed by known methods, e.g., Scatchard analysis. Ideally, the antigen-binding affinity of the humanized antibody will approximate that of the parent antibody, e.g., 64G12., or will retain at least 50% of the binding affinity of the parent antibody (i.e., the antibody that donated the CDRs).

An antibody can be humanized by any method, which is capable of replacing at least a portion of a CDR of a human antibody with a CDR derived from a nonhuman antibody. Winter describes a method which may be used to prepare the humanized antibodies of the present invention (UK Patent Application GB 2188638A, filed on Mar. 26, 1987), the contents of which is expressly incorporated by reference. The human CDRs may be replaced with nonhuman CDRs, for example using oligonucleotide site-directed mutagenesis as described in International Application WO 94/10332 entitled, *Humanized Antibodies to Fc Receptors for Immunoglobulin G on Human Mononuclear Phagocytes*.

Also within the scope of the invention are chimeric and humanized antibodies in which specific amino acids have been substituted, deleted or added. In particular, preferred humanized antibodies have amino acid substitutions in the framework region, such as to improve binding to the antigen. For example, in a humanized antibody having mouse CDRs, amino acids located in the human framework region can be replaced with the amino acids located at the corresponding positions in the mouse antibody. Such substitutions are known to improve binding of humanized antibodies to the antigen in some instances. Antibodies in which amino acids have been added, deleted, or substituted are referred to herein as modified antibodies or altered antibodies.

The present invention further embraces variants and equivalents which are substantially homologous to the humanized antibodies and antibody fragments set forth herein. These may contain, e.g., conservative substitutions, i.e. the substitution of one or more amino acids by similar amino acids. For example, conservative substitution refers to the substitution of an amino acid with another within the same general class, e.g., one acidic amino acid with another acidic amino acid, one basic amino acid with another basic amino acid, or one neutral amino acid by another neutral amino acid. What is intended by a conservative amino acid substitution is well known in the art.

The phrase "substantially homologous" is used in regard to the similarity of a subject amino acid sequence (of an oligo- or poly-peptide or protein) to a related, reference amino acid sequence. This phrase is defined as at least about 75% "correspondence"—i.e. the state of identical amino acid residues being situated in parallel—between the subject and reference sequences when those sequences are in "alignment," i.e. when a minimal number of "null" bases have been inserted in the subject and/or reference sequences so as to maximize the number of existing bases in correspondence between the sequences. "Null" bases are not part of the subject and reference sequences; also, the minimal number of "null" bases inserted in the subject sequence may differ from the minimal number inserted in the reference sequence. In this definition, a reference sequence is considered "related" to a subject sequence where both amino acid sequences make up proteins or portions of proteins which are either αIFNAR-1 antibodies or antibody fragments with αIFNAR-1 binding affinity. Each of the proteins comprising these αIFNAR-1 antibodies or antibody fragments may independently be antibodies or antibody fragments or bi- or multi-functional proteins, e.g., such as fusion proteins, bi- and multi-specific antibodies, single chain antibodies, and the like.

One skilled in the art would be able (by routine experimentation) to determine what amount of antibody would be effective and non-toxic for the purpose of treating autoimmune diseases or for prevention of transplant rejection. Generally, however, an effective dosage will be in the range of about 0.05 to 100 milligrams per kilogram body weight per day.

The humanized antibodies or humanized antibody fragments of the invention may be administered to a subject in accordance with the aforementioned methods of treatment in an amount sufficient to produce a therapeutic or prophylactic effect. The antibodies of the subject invention can be administered to such human or other animal in a conventional dosage form prepared by combining the antibody of the invention with a conventional, pharmaceutically acceptable carrier, diluent, and/or excipient according to known techniques. It will be recognized by one of ordinary skill in the art that the form and character of the pharmaceutically acceptable carrier, diluent, and/or excipient is dictated by the amount of active ingredient with which it is to be combined, the route of administration, and other well-known variables.

The route of administration of the antibodies (or fragment thereof) of the present invention may be oral, parenteral, by inhalation, or topical. The term parenteral as used herein includes intravenous, intramuscular, subcutaneous, rectal, vaginal, or intraperitoneal administration. The subcutaneous, intravenous, and intramuscular forms of parenteral administration are generally preferred.

Generation of Transfectomas Producing Humanized Monoclonal Antibodies to IFNAR-1

Humanized antibodies of the invention also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification, site directed mutagenesis) and can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to includes promoters, enhancers and other expression control elements (e.g., polyadenylation signals) that control the transcription or translation of the antibody chain genes. Such regulatory sequences are described, for example, in Goeddel; Gene Expression Technology. Methods in Enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter or β-globin promoter.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like.

Preferred mammalian host cells for expressing the recombinant antibodies of the invention include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NS0 myeloma cells, COS cells and SP2 cells. In particular, for use with NS0 myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Pharmaceutical Compositions

In another aspect, the present invention provides a composition, e.g., a pharmaceutical composition, containing one or a combination of humanized monoclonal antibodies, or antigen-binding portion(s) thereof, of the present invention, formulated together with a pharmaceutically acceptable carrier. Such compositions may include one or a combination of (e.g., two or more different) humanized antibodies of the invention.

In one embodiment, the invention provides a therapeutic composition comprising a combination of humanized anti-IFNAR-1 antibodies which bind to different epitopes on human IFNAR-1 and have complementary activities, e.g., as a pharmaceutical composition. Furthermore, a humanized antibody of the invention can be conjugated to a therapeutic agent, such as a toxin or radiolabel, to form an immunoconjugate or can be linked to one or more additional antibodies to form a bispecific (or multispecific) molecule. In another embodiment, the therapeutic composition comprises one or a combination of immunoconjugates or bispecific (or multispecific) molecules of the invention.

Pharmaceutical compositions of the invention also can be administered in combination therapy, i.e., combined with other agents. For example, the combination therapy can include a composition of the present invention with at least one other therapy.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine. N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion.

Preferred routes of administration for the antibody compositions of the invention are intravenously, intramuscularly and intraperitoneally. Preferred modes of delivery are by injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, for example to humans or animals, they can be given alone or as a pharmaceutical composition containing, for example, 0.01 to 99.5% (more preferably, 0.1 to 90%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic compositions may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the humanized monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134), different species of which may comprise the formulations of the inventions, as well as components of the invented molecules; p120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a desired site. The composition must be fluid to the extent that easy syringability exists. It must be stable under the conditions of manufacture and storage and must be preserved against the contaminating action of microorganisms such as bacteria and fungi.

A "therapeutically effective dosage" preferably inhibits the biological activity of Type I interferons by at least about 20%, more preferably by at least about 40%, even more preferably by at least about 60%, and still more preferably by at least about 80% relative to untreated subjects. The ability of a compound to inhibit the biological activity of Type I interferons can be evaluated in an animal model system, such as those described in the Examples or other model systems known in the art that are predictive of efficacy in human conditions associated with aberrant Type I interferon activity. Alternatively, this property of a composition can be evaluated by examining the ability of the compound to inhibit the biological activity of Type I interferons. Such inhibition can be determined using in vitro assays known to the skilled practitioner, including but not limited to the in vitro assays described in the Examples. A therapeutically effective amount of a therapeutic compound can inhibit Type I interferon activity such that the symptoms of a disease or disorder mediated, at least in part, by aberrant Type I interferon expression or activity, are ameliorated. Such diseases and disorders include autoimmune diseases, transplant rejection and GVHD. One of ordinary skill in the art would be able to determine such amounts based on such factors as the subject's size, the severity of the subject's symptoms, and the particular composition or route of administration selected.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

Uses and Methods of the Invention

Humanized monoclonal anti-IFNAR-1 antibodies and related derivatives/conjugates and compositions of the present invention have a variety of in vitro and in vivo diagnostic and therapeutic utilities. For example, these molecules can be administered to cells in culture, e.g. in vitro or ex vivo. Alternatively, they can be administered to a subject, e.g., in vivo, to treat, prevent or diagnose a variety of disorders in which type I interferon plays a role. As used herein, the term "subject" is intended to include both human and nonhuman animals. The term "nonhuman animals" of the invention includes all vertebrates, e.g., mammals and non-mammals, such as nonhuman primates, sheep, dog, cow, chickens, amphibians, reptiles, etc.

The antibody compositions of the invention can be used in the treatment of autoimmune diseases, such as systemic lupus erythematosus (SLE), inflammatory bowel disease (IBD; including Crohn's Disease, Ulcerative Colitis and Celiac's Disease), insulin dependent diabetes mellitus (IDDM) and rheumatoid arthritis (RA). Furthermore, the antibody compositions of the invention can be used for inhibiting or preventing transplant rejection or in the treatment of graft versus host disease (GVHD).

Uses of the antibody compositions of the invention to treat inflammatory bowel disease are described in detail in the co-owned U.S. patent application entitled "Compositions and Methods for the Therapy of Inflammatory Bowel Disease" having U.S. Ser. No. 60/465,155, filed on Apr. 23, 2003, the entire contents of which are expressly incorporated herein by reference.

Human antibodies of the invention can be initially tested for binding activity associated with therapeutic use in vitro. For example, compositions of the invention can be tested using Biacore and flow cytometric assays described in the Examples below. Suitable methods for administering antibodies and compositions of the present invention are well known in the art. Suitable dosages also can be determined within the skill in the art and will depend on the age and weight of the subject and the particular drug used.

Human anti-IFNAR-1 antibodies of the invention also can be co-administered with other therapeutic agents as described above.

Preferred are pharmaceutical preparations for parenteral administration, such as are described in Remington's Pharmaceutical Sciences, Mack Publishing Co., Easton, Pa., 1989. The final preparations contain from 0.01 t to 50% of active ingredients. Methods for the production of such conjugates and their use in diagnostics and therapeutics are provided in, for example, Shih et al., U.S. Pat. No. 5,057,313; Shih et al., Int. J. Cancer 41:832 (1988); copending, commonly owned U.S. Ser. No. 08/162,912; and, McKearn et al., U.S. Pat. No. 5,156,840, the contents of which are incorporated by reference.

As noted above, for purposes of therapy, a humanized antibody compositions and a pharmaceutically acceptable carrier are administered to a patient in a therapeutically effective amount. A combination of an antibody composition and a pharmaceutically acceptable carrier is said to be administered in a "therapeutically effective amount" if the amount administered is physiologically significant. An agent is "physiologically significant" if its presence results in a detectable change in the physiology of a recipient patient. A targeted therapeutic agent is "therapeutically effective" if it delivers a higher proportion of the administered dose to the intended target than accretes at the target upon systemic administration of the equivalent untargeted agent.

The present invention is further illustrated by the following examples which should not be construed as further limiting. The contents of all figures and all references, patents and published patent applications cited throughout this application are expressly incorporated herein by reference.

EXAMPLE 1

Production of Humanized Antibodies Specific for IFNAR-1

The source of the donor CDRs used to prepare the humanized antibody was a murine monoclonal antibody, 64G12, which is specific for IFNAR-1 (U.S. Pat. No. 5,919,453). A 64G12 hybridoma cell line was previously established.

Cloning of 64G12 Variable Regions mRNA was extracted from the 64G12 hybridoma using Qiagen's Oligotex mRNA Miniprep Kit and the subsequent cDNA was synthesized using Clontech's Marathon cDNA Amplification Kit. The variable regions for the heavy chains of 64G12 were amplified with Qiagen's HotStarTaq using primers against the murine IgG1 gene (Forward: ATGGGCA-GACTTACATTCTCATTCCTG (SEQ ID NO:43) and Reverse: CAGTGGATAGACAGATGGGG) (SEQ ID NO:44) while the light chains were amplified using primers against the murine kappa gene (ACTGGATGGTGGGAA-GATGG) (SEQ ID NO:45) and the N-terminal amino acid sequence (CTCACCCAGTCTCCAACCACCATGGCTG-CATC) (SEQ ID NO:46). The identity of the chains was confirmed by comparing the peptide sequence from the N-terminus of the 64G12 antibody with the translated protein sequence from the cDNA clones.

Construction of Variable Regions

From the sequences of the 64G12 VH and VL domains the CDR sequences were determined with reference to the database of Kabat et al. ("Sequences of Proteins of Immunological Interest" US Department of Health and Human Services, US Government Printing Office), the contents of which is expressly incorporated by reference, and utilizing computer assisted alignment with other VH and VL sequences. The VH sequence is shown in SEQ ID NO:7. The VL sequence is shown in SEQ ID NO:19. The amino acid sequences of the CDR regions of the VH and VL domains are shown in Table 1 below.

TABLE 1

| SEQ ID NO: | SEQUENCE | DESCRIPTION |
|---|---|---|
| 1 | TSGMGIG | 64G12 $V_H$ CDR1 |
| 2 | HIWWDDDKYYNPSLKS | 64G12 $V_H$ CDR2 |
| 3 | NYYPYDAWFDY | 64G12 $V_H$ CDR3 |
| 4 | SASSSINSNHLH | 64G12 $V_L$ CDR1 |

TABLE 1-continued

| SEQ ID NO: | SEQUENCE | DESCRIPTION |
|---|---|---|
| 5 | RTSILAS | 64G12 $V_L$ CDR2 |
| 6 | QQGSNIIPFT | 64G12 $V_L$ CDR3 |

The murine variable regions were amplified from the templates mention above using primers with the restriction sites that allowed in-frame subcloning into our mammalian expression vectors.

The first series human variable region cDNA's were synthesized by Operon. Subsequent deimmunized antibodies were created with Stratagene's QuikChange Site-directed Mutagenesis kit.

Expression of Full-Length Antibodies

All heavy and light variable region sequences (murine and human) were subcloned in-frame with the human IgG constant regions into Invitrogen's mammalian expression vectors pcdna3.1/neo and pcdna3.1/hygro, respectively. The human osteonectin signal sequence was used in place of the endogenous IgG sequence to secrete the recombinant antibodies. Furthermore, the 4.2 kb RNP UCOE's (Benton et al., Cytotechnology, 38:43-46,2002) were inserted upstream of the CMV promoters to maintain open chromatin and allow rapid generation of cells expressing high levels of antibodies.

For transient transfections, human 293 cells were co-transfected with both heavy and light chain carrying plasmids using Roche's FuGENE 6. Supernatants were collected 3-4 days post transfection and the antibodies were purified via protein A-sepharose chromatography.

For stable expression, CHO-S cells were co-transfected with both heavy and light chain carrying linearized plasmids using Invitrogen's DMRIE-C. Stably transfected cells were selected by adding Geneticin and Hygromycin B at 500 ug/mL to the growth media. The antibody secreting cells were expanded and antibody was purified from the culture medium by protein A affinity chromatography as described by Harlow and Lane (Antibodies: A Laboratory Manual, Cold Spring Harbor Laboratory, Cold Spring Harbor, N.Y.), the contents of which is expressly incorporated by reference.

Transfer of the murine 64G12 CDRs to human frameworks was achieved by oligonucleotide site-directed mutagenesis as described by Nakamye et al. (Nucleic Acids Res 14, 9679-9687 (1986)), the contents of which is expressly incorporated by reference. The DNA templates used for mutagenesis of VHs comprised human framework regions from the human germline sequences DP-26, DP-47, and DPk26, as follows:

```
(DP-26) (Genbank: HSIGDP26)
                                        (SEQ ID NO:47)
QVTLKESGPVLVKPTETLTLTCTVSGFSLSNARMGVSWIRQPPGKALEWL

AHIFSNDEKSYSTSLKSRLTISKDTSKSQVVLTMTNMDPVDTATYY, (DP-47) (Genbank: HSIGDP47)
                                        (SEQ ID NO:48)
EVQLLESGGGLVQPGGSLRLSCAASGFTFSSYAMSWVRQAPGKGLEWVSA ISGSGGSTYYADSVKGRFTISRDNSKNTLYLQMNSLRAEDTAVYYCAK,
and (DPk26) (Genbank: HSIGDPK26)
                                        (SEQ ID NO:49)
EIVLTQSPDFQSVTPKEKVTITCRASQSIGSSLHWYQQKPDQSPKLLIKY

ASQSFSGVPSRFSGSGSGTDFTLTINSLEAEDAATYYCHQSSSLP.
```

Furthermore, in certain constructs, additional substitutions were made in CDR and/or FR residues for purposes of increasing binding affinity or decreasing antibody immunogenicity (discussed further below).

In summary, a series of humanized antibody heavy and light chain variable regions were made, comprising sequences as follows. The amino acid sequences of these antibody heavy and light chain variable regions are shown in FIGS. 1B-1L and 2B-2S, along with the amino acid sequence of the donor murine 64G12 variable regions (the 64G12 VH sequence is SEQ ID NO:7 of FIG. 1A and the 64G12 VL sequence is SEQ ID NO:19 of FIG. 2A).

Heavy chain sequence H2 was designed by combining the CDRs of 64G12 VH with the human immunoglobulin heavy chain germline DP-28 framework sequence (SEQ ID NO:8 of FIG. 1B).

Heavy chain sequence H2-C3 was designed by combining only the CDR3 of 64G12 VH with the human immunoglobulin heavy chain germline DP-28 framework sequence (SEQ ID NO:9 of FIG. 1C).

Heavy chain sequence H3 was designed by combining the CDRs of 64G12 VH with a consensus human immunoglobulin heavy chain framework sequence (SEQ ID NO:10 of FIG. 1D).

Heavy chain sequence M3 was designed by combining the CDRs of 64G12 VH with the human immunoglobulin heavy chain germline DP-47 framework sequence (SEQ ID NO:11 of FIG. 1E).

Heavy chain sequence M3-4 was designed from the M3 sequence, in which position 4 of CDR3 was substituted with one of the following amino acids: L, N, E, V, A, C, G, S, R, D, M, H, T, W, K or I (SEQ ID NO:12 of FIG. 1F).

Heavy chain sequence M3-11 was designed from the M3 sequence, in which position 11 of CDR3 was substituted with one of the following amino acids: L, E, Q, R, V, A, F, G, C, T, W, H, K, D, S or I (SEQ ID NO:13 of FIG. 1G).

Heavy chain sequence M3-A was designed from the M3 sequence, in which a T cell epitope was removed by substituting the amino acid at position 4 of CDR1 (a methionione) with an alanine (SEQ ID NO:14 of FIG. 1H).

Heavy chain sequence M3-B was designed from the M3 sequence, in which a T cell epitope was removed by substituting the amino acid at position 16 of CDR2 (a serine) with an alanine (SEQ ID NO:15 of FIG. 1I).

Heavy chain sequence M3-A/B was designed from the M3 sequence, in which both the substitutions from M3-A and M3-B were incorporated into the sequence (SEQ ID NO:16 of FIG. 1J).

Heavy chain sequence DI M3 was designed from the M3 sequence, in which all of its potential T cell epitopes were removed by making substitutions at six framework residues (SEQ ID NO:17 of FIG. 1K).

Heavy chain sequence DI M3-B was designed from the M3 sequence, in which the framework substitutions from the DI M3 sequence and the CDR2 substitution from the M3-B sequence were combined (SEQ ID NO:18 of FIG. 1L).

Light chain sequence K6 was designed by combining the CDRs of 64G12 VL with the human immunoglobulin light chain germline DPk-26 framework sequence (SEQ ID NO:20 of FIG. 2B).

Light chain sequence K1 was designed by combining the CDRs of 64G12 VH with a consensus human immunoglobulin light chain framework sequence (SEQ ID NO:21 of FIG. 2C).

Light chain sequence K1-C was designed from the K1 sequence, in which one of its potential T cell epitopes was removed by substituting position 4 of CDR1 (a serine) with a threonine (SEQ ID NO:22 of FIG. 2D).

Light chain sequence K1-D was designed from the K1 sequence, in which one of its potential T cell epitopes was removed by substituting position 12 of CDR1 (a histidine) with an asparagine (SEQ ID NO:23 of FIG. 2E).

Light chain sequence K1-E was designed from the K1 sequence, in which one of its potential T cell epitopes was removed by substituting position 3 of CDR3 (a glycine) with a threonine (SEQ ID NO:24 of FIG. 2F).

Light chain sequences K1-C/D, K1-C/E, K1-D/E and K1-C/D/E were designed from the K1 sequence, in which the substitutions from K1-C and K1-D, the substitutions from K1-C and K1-E, the substitutions from K1-D and K1-E and the substitutions from K1-C, K1-D and K1-E were combined, respectively (SEQ ID NO:25, SEQ ID NO:26, SEQ ID NO:27, and SEQ ID NO:28, respectively, of FIGS. 2G, 2H, 2I, and 2J).

Light chain sequence DI K1 was designed from the K1 sequence, in which all of its potential T cell epitopes were removed by making substitutions at six framework residues (SEQ ID NO:29 of FIG. 2K).

Light chain sequence DI K1-C was designed from the K1 sequence, combining the framework substitutions from DI K1 with the substitution in CDR1 from K1-C (SEQ ID NO:30 of FIG. 2L).

Light chain sequence DI K1-DS was designed from the K1 sequence, in which five of the six potential T cell epitopes were removed by making substitutions in five framework residues (SEQ ID NO:31 of FIG. 2M).

Light chain sequence DI K1-C-DS was designed from the K1 sequence, in which the substitutions from DI K1-DS and the substitution from K1-C were combined (SEQ ID NO:32 of FIG. 2N).

Light chain sequences DI K1-A19V, DI K1-L37Q, DI K-1-A46L, DI K1-I58V and DI K1-T83F were designed from the K1 sequence, in which five of the six potential T cell epitopes were removed by changing the highlighted amino acids in the framework region as shown in SEQ ID NO:33, SEQ ID NO:34, SEQ ID NO:35, SEQ ID NO:36, and SEQ ID NO:37 of FIGS. 2O, 2P, 2Q, 2R, and 2S, respectively.

FIGS. 3A-3D show the nucleic acid sequences of heavy chain variable regions M3 (FIG. 3A) and DI M3-B (FIG. 3C) and of light chain variable regions K1 (FIG. 3B) and K1-C (FIG. 3D).

EXAMPLE 2

Biacore Analysis of Certain Humanized $V_H$ and $V_L$ Pairings

A series of humanized antibody $V_H$ and $V_L$ pairings were produced and compared to the original murine antibody, as well as a mouse-human chimeric antibody which contained the murine variable regions from 64G12 and human IgG4 kappa constant regions. Human heavy chains H2 and H3 were expressed in combination with human light chains K1 and K6 to make the antibodies H2K6, H2K1, H3K6 and H3K1. The amino acid sequences of these variable regions are shown in FIGS. 1B, 1D, 2B, and 2C.

Antibodies from clones 64G12, H2K6, H2K1, H3K6, and H3K1 were assayed by Biacore analysis (Biacore AB, Uppsala, Sweden) to determine binding kinetics. Purified recombinant IFNAR-1 extracellular fragment was coupled to the CM5 sensor chip @ 600 RU. Binding was measured by adding antibody at concentrations from 1.75-80 nM at a flow rate of 20 ul/min. The binding curves were fit to a Langmuir binding model using BIAevaluation software (Biacore AB, Uppsala, Sweden). Determined $K_D$ values are shown in Table 2:

TABLE 2

| Antibody | $K_D$ (M) |
|---|---|
| 64G12 (mouse IgG1) | $1.2 \times 10^{-9}$ |
| Chimeric IgG4 | $3.6 \times 10^{-9}$ |
| H2K6 | $1.3 \times 10^{-9}$ |
| H2K1 | $0.8 \times 10^{-9}$ |
| H3K6 | $1.8 \times 10^{-9}$ |
| H3K1 | $3.4 \times 10^{-9}$ |

Binding affinity of the murine antibody standard and the human IgG4 chimeric antibody were determined to be in the range of 1.2-3.6 nM using this assay. All of the humanized antibody combinations led to antibodies with high binding affinity to IFNAR-1, indistinguishable from the chimeric antibody and original murine hybridoma derived antibody 64G12.

An alternate heavy chain termed H2-C3 (SEQ ID NO:9 of FIG. 1C), in which only CDR3 was preserved from the murine antibody, was also expressed in combination with the K6 light chain but the antibody produced was not able to bind IFNAR-1.

Another humanized heavy chain, termed M3 (SEQ ID NO:11 of FIG. 1E, which comprises the human immunoglobulin heavy chain germline DP-47 framework sequence) was co-expressed with the K1 light chain and also resulted in an antibody capable of high affinity binding to IFNAR-1. The binding affinity was determined using a capture assay in which anti-human IgG Fc was immobilized on a Biacore chip, the human anti-IFNAR-1 antibodies were captured by passing them over the anti-human IgG Fc surface and then soluble IFNAR-1 binding was measured at concentrations from 25-400 nM to enable binding affinity to be calculated. The binding affinity of M3K1 was compared to that of H3K1. The results are shown in Table 3:

TABLE 3

| | ka (1/Ms) | kd (1/s) | $K_D$ (M) |
|---|---|---|---|
| H3K1 | 8.06E+03 | 5.04E−05 | 6.26E−09 |
| M3K1 | 5.34E+03 | 3.79E−05 | 7.09E−09 |
| Flow cell 2-1, low density capture | | | |
| H3K1 | 7.48E+03 | 4.81E−05 | 6.43E−09 |
| M3K1 | 5.49E+03 | 4.39E−05 | 7.99E−09 |
| Flow cell 4-3, higher density capture | | | |

EXAMPLE 3

Deimmunization of Selected Antibody Sequences

The H3K1 VH and VK sequences were analyzed using a Peptide Threading program (Biovation, Inc.). Briefly, the amino acid sequences are divided into all possible 13-mers. The 13-mer peptides are sequentially presented to the modules of the binding groove of the HLA-DR allotypes and a binding score assigned to each peptide for each allele. A conformational score is calculated for each pocket-bound side chain of the peptide. This score is based on steric overlap, potential hydrogen bonds between peptide and residues in the binding groove, electrostatic interactions and favorable contacts between peptide and pocket residues. The conformation of each side chain is then altered and the score recalculated.

Potential T cell epitopes are removed by making amino acid substitutions in the particular peptide that constitutes the epitope. Substitutions were made by inserting amino acids of similar physicochemical properties if possible. However, in order to remove some potential epitopes, amino acids of different size, charge or hydrophobicity may need to be substituted. Numbering of amino acid residues for substitution is as per Kabat (Kabat et al, 1991). The amino acid substitutions are summarized and illustrated in FIGS. 1H-1L and 2D-2S.

A series of antibodies were constructed with reduced numbers of potential T-cell epitopes. These included heavy chain variants M3-A and M3-B in which residues were changed in CDR regions and DI M3 in which framework residues were altered. De-immunized light chains were also constructed termed K1-C, K1-D, K1-E and DI K1. These deimmunized V-regions were expressed as human IgG4 antibodies in various combinations as shown in Table 4. The antibodies were expressed and purified before analysis by Biacore. A Biacore chip was used with IFNAR-1 coated on Flow cell 2 at 690 RU and anti-human IgG Fc on flow cell 4 at 5000 RU. Binding of the antibody to IFNAR-1 relative to anti-human IgG Fc was determined by the ratio of response at flow cell 2 divided by flow cell 4 (Fc2/Fc4). Several variants retained high IFNAR-1 binding activity compared to the H3K1 standard as also shown in Table 4.

TABLE 4

| Heavy chain | | Light Chain | | | % activity relative to |
|---|---|---|---|---|---|
| Name | SEQ ID NO: | Name | SEQ ID NO: | Fc2/Fc4 | H3K1 |
| H3 | 10 | K1 | 21 | 0.30 | 100 |
| M3 | 11 | K1 | 21 | 0.42 | 140 |
| DI M3 | 17 | K1 | 21 | 0.41 | 137 |
| M3 | 11 | DI K1 | 29 | 0.17 | 57 |
| DI M3 | 17 | DI K1 | 29 | 0.06 | 20 |
| M3-A | 14 | K1 | 21 | 0.05 | 17 |
| M3-B | 15 | K1 | 21 | 0.31 | 103 |
| M3-AB | 16 | K1 | 21 | 0.13 | 43 |
| M3 | 11 | K1-C | 22 | 0.29 | 97 |
| M3 | 11 | K1-D | 23 | 0.09 | 30 |
| M3 | 11 | K1-E | 24 | −0.05 | — |
| M3 | 11 | K1-CD | 25 | 0.17 | 57 |
| M3 | 11 | K1-CDE | 28 | −0.10 | — |
| M3 | 11 | K1-DE | 27 | −0.10 | — |
| M3-AB | 16 | K1-CD | 25 | 0.07 | 23 |

Additional combination variants heavy chain DI M3-B and light chain DI K1-C were also made. These combination variants were also tested for binding to IFNAR-1. Results demonstrated that although high binding affinity was retained with the DI M3-B heavy chain, the use of the DI K1-C light chain resulted in reduced binding activity, similar to that seen with the DI K1 light chain. The results are shown in Table 5. Binding analysis was done by Biacore, with the antibody bound to immobilized soluble IFNAR-1. Maximal response was determined at two concentrations and values shown are mean of four determinations.

TABLE 5

| Heavy chain | | Light Chain | | % response |
|---|---|---|---|---|
| Name | SEQ ID NO: | Name | SEQ ID NO: | relative to H3K1 |
| H3 | 10 | K1 | 21 | 100 |
| M3 | 11 | K1 | 21 | 97 |
| M3-B | 15 | K1 | 21 | 117 |

TABLE 5-continued

| Heavy chain | | Light Chain | | % response |
|---|---|---|---|---|
| Name | SEQ ID NO: | Name | SEQ ID NO: | relative to H3K1 |
| DI M3 | 17 | K1 | 21 | 149 |
| DI M3-B | 18 | K1 | 21 | 122 |
| M3 | 11 | K1-C | 22 | 100 |
| M3-B | 15 | K1-C | 22 | 156 |
| DI M3 | 17 | K1-C | 22 | 96 |
| DI M3-B | 18 | K1-C | 22 | 100 |
| M3 | 11 | DI K1 | 29 | 25 |
| M3-B | 15 | DI K1 | 29 | 17 |
| DI M3 | 17 | DI K1 | 29 | 8 |
| DI M3-B | 18 | DI K1 | 29 | 11 |
| M3 | 11 | DI K1-C | 30 | 17 |
| M3-B | 15 | DI K1-C | 30 | 14 |
| DI M3 | 17 | DI K1-C | 30 | 4 |
| DI M3-B | 18 | DI K1-C | 30 | 9 |

To further characterize selected variants their affinity was determined using the antibody capture assay (in which anti-human IgG Fc was bound to the Biacore chip and soluble IFNAR-1 was used at 25-400 nM). Results are shown in Table 6 and demonstrate that high binding affinity to IFNAR was seen with these variants.

TABLE 6

| | ka (1/Ms) | kd (1/s) | $K_D$ (M) | Ab Rmax |
|---|---|---|---|---|
| M3 K1 | 5.34E+03 | 3.79E−05 | 7.09E−09 | 528 |
| M3-B K1-C | 5.49E+03 | 4.10E−05 | 7.47E−09 | 520 |
| DIM3-B K1-C | 5.61E+03 | 2.82E−06 | 5.02E−10 | 479 |
| Flow cell 2-1, low density capture | | | | |
| M3K1 | 5.49E+03 | 4.39E−05 | 7.99E−09 | 924 |
| M3-B K1-C | 5.46E+03 | 4.06E−05 | 7.45E−09 | 908 |
| DIM3-B K1-C | 4.64E+03 | 1.64E−05 | 3.53E−09 | 848 |
| Flow cell 4-3, higher density capture | | | | |
| Capture by anti-human IgG Fc, soluble IFNAR (25-400 nM) | | | | |

EXAMPLE 4

Alteration of CDR Residues in Selected Antibody Sequences

A series of alternate heavy chains were produced with altered CDR3 sequences. A series of pools, each of which contained multiple amino acid substitutions at one of the 11 positions in CDR3, were co-expressed with the K1 light chain and antibody from each pool purified for testing. Biacore experiments were carried out to determine binding activity to immobilized soluble IFNAR-1. The CDR3 variant libraries of anti-IFNAR-1 antibodies was determined by binding the pool of antibodies to immobilized soluble IFNAR-1. Response units were generated from 200 nM samples (A: RU at max association; D: RU after 800 seconds dissociation). As shown in Table 7, varying levels of activity were determined for each pool.

TABLE 7

| Antibody Heavy chain | Heavy chain CDR3 | A: RU at max association | D: RU after 800 seconds dissociation | Max Response relative to H3K1 (%) |
|---|---|---|---|---|
| H3(sequence 10) | As in SEQ ID NO: 10 | 194 | 190 | 100 |
| M3-1 | CDR3 aa1 randomized | 74 | 61 | 38 |
| M3-2 | CDR3 aa2 randomized | 147 | 140 | 76 |
| M3-3 | CDR3 aa3 randomized | 98 | 88 | 51 |
| M3-4 | CDR3 aa4 randomized | 102 | 89 | 53 |
| M3-5 | CDR3 aa5 randomized | 60 | 41 | 31 |
| M3-6 | CDR3 aa6 randomized | 21 | 12 | 11 |
| M3-7 | CDR3 aa7 randomized | 104 | 99 | 54 |
| M3-8 | CDR3 aa8 randomized | 26 | 19 | 14 |
| M3-9 | CDR3 aa9 randomized | 87 | 83 | 45 |
| M3-10 | CDR3 aa10 randomized | 45 | 38 | 23 |
| M3-11 | CDR3 aa11 randomized | 149 | 146 | 77 |

Pools 4 and 11 were selected for further study and the individual antibodies in each pool were produced and expressed separately. The sequences of these individual antibodies were as shown in SEQ ID NO:12 of FIG. 1F and SEQ ID NO: 13 of FIG. 1G. Biacore analysis of binding of the individual antibodies in pool 4 to IFNAR-1 is shown in Table 8. The data is presented as maximal association relative to M3K1. Biacore analysis of binding of the individual antibodies in pool 11 to IFNAR-1 is shown in Table 9. The data is presented as maximal association relative to M3K1.

TABLE 8

| Heavy Chain | | X amino | Light chain | | % activity |
|---|---|---|---|---|---|
| Name | SEQ ID NO: | acid residue | Name | SEQ ID NO: | relative to M3K1 |
| H3 | 10 | — | K1 | 21 | 115 |
| M3 | 11 | — | K1 | 21 | 100 |
| M3-4 | 12 | L | K1 | 21 | 126 |
| M3-4 | 12 | N | K1 | 21 | 49 |
| M3-4 | 12 | E | K1 | 21 | 128 |
| M3-4 | 12 | V | K1 | 21 | 122 |
| M3-4 | 12 | A | K1 | 21 | 107 |
| M3-4 | 12 | C | K1 | 21 | 123 |
| M3-4 | 12 | G | K1 | 21 | 114 |
| M3-4 | 12 | S | K1 | 21 | 110 |
| M3-4 | 12 | I | K1 | 21 | 106 |
| M3-4 | 12 | R | K1 | 21 | 106 |
| M3-4 | 12 | D | K1 | 21 | 100 |
| M3-4 | 12 | M | K1 | 21 | 101 |
| M3-4 | 12 | H | K1 | 21 | 79 |
| M3-4 | 12 | T | K1 | 21 | 103 |
| M3-4 | 12 | W | K1 | 21 | 93 |
| M3-4 | 12 | K | K1 | 21 | 86 |

TABLE 9

| Heavy Chain | | X amino | Light chain | | % activity |
|---|---|---|---|---|---|
| Name | SEQ ID NO: | acid residue | Name | SEQ ID NO: | relative to M3K1 |
| H3 | 10 | — | K1 | 21 | 138 |
| M3 | 11 | — | K1 | 21 | 100 |
| M3-11 | 13 | L | K1 | 21 | 75 |
| M3-11 | 13 | E | K1 | 21 | 105 |
| M3-11 | 13 | Q | K1 | 21 | 73 |
| M3-11 | 13 | R | K1 | 21 | 220 |
| M3-11 | 13 | V | K1 | 21 | 108 |
| M3-11 | 13 | A | K1 | 21 | 93 |
| M3-11 | 13 | F | K1 | 21 | 93 |
| M3-11 | 13 | G | K1 | 21 | 63 |

TABLE 9-continued

| Heavy Chain | | X amino | Light chain | | % activity |
|---|---|---|---|---|---|
| Name | SEQ ID NO: | acid residue | Name | SEQ ID NO: | relative to M3K1 |
| M3-11 | 13 | C | K1 | 21 | 64 |
| M3-11 | 13 | I | K1 | 21 | 81 |
| M3-11 | 13 | T | K1 | 21 | 82 |
| M3-11 | 13 | W | K1 | 21 | 70 |
| M3-11 | 13 | H | K1 | 21 | 104 |
| M3-11 | 13 | K | K1 | 21 | 82 |
| M3-11 | 13 | D | K1 | 21 | 67 |
| M3-11 | 13 | S | K1 | 21 | 39 |

Binding to IFNAR-1 was maintained by all of the variants produced with varying antigen binding activities as shown in tables 8 and 9.

EXAMPLE 5

Scatchard Binding Analysis of Anti-IFNAR-1 Humanized Antibodies to Cells

BALL-1 cells, which express IFNAR-1 and IFNAR-2, were used to assess the binding of anti-IFNAR-1 humanized antibodies to cells by Scatchard analysis. The cells were grown in RPMI containing 10% FCS and washed twice with Hanks Balanced Salt Solution (HBSS) at 4 degrees C. The cells were adjusted to $4\times10^7$ cells/ml in Tris binding buffer (24 mM Tris, 137 mM NaCl, 2.7 mM KCl, 0.1% HSA, 2 mM glucose, 1 mM $MgCl_2$, 1 mM $CaCl_2$, pH 7.4). Millipore plates (MAFB NOB) were coated with 1% nonfat dry milk in water and stored a 4° C. overnight. The plates were washed with binding buffer and 25 ul of unlabeled antibody (1000-fold excess) in TBS binding buffer was added to control wells in a Millipore 96 well glass fiber filter plate (non-specific binding NSB). Twenty-five microliters of buffer alone was added to the maximum binding control well (total binding). Twenty-five microliters of $^{125}$I-anti-IFNAR-1 antibody and 25 ul of BALL-I cell suspension ($4\times10^7$ cells/ml) in TBS binding buffer were added. The plates were incubated for 2 hours at 200 RPM on a shaker at 4° C. At the completion of the incubation the Millipore plates were washed twice with 0.2 ml of cold TBS binding buffer containing a final concentration of 0.5 M NaCl. The filters were removed and counted in a gamma counter. Evaluation of equilibrium binding was performed using single site binding parameters with the Prism software (San Diego, Calif.).

Using the above scatchard binding assay, the affinity of the humanized antibody H3K1 (IgG4 isotype) for BALL-1 cells was 4 nM which is very similar to the murine 64G12. The low nanomolar affinity values obtained with the whole cell-binding assay are comparable to Biacore data in which the affinity of the antibody to the purified recombinant ligand is determined (Table 10). Therefore in either a protein-based or cell-based assay, the binding affinity of the antibodies are in the low nM range.

TABLE 10

| | Isotype | Receptor Binding (Biacore) $K_D$ (nM) | Cell Binding affinity (BALL-1) $K_D$ (nM) |
|---|---|---|---|
| 64G12 | m IgG1 | 1.2 | 3.9 |
| H3K1 | h IgG4 | 3.4 | 4.0 |

EXAMPLE 6

Anti-IFNAR-1 Humanized Antibodies Inhibit the Biological Activity of Type I IFNs in Cell Proliferation and IFN-Responsive Reporter Assays The cell line Daudi, derived from a human B-lymphoblast Burkitt's lymphoma, expresses high levels of IFNAR, and the growth of these cells is inhibited by type I interferons. To measure the functional blocking ability of humanized anti-IFNAR-1 antibodies two different assays were performed. In the first assay, Daudi cells were cultured with interferon α2b in the presence or absence of antibody and proliferation was measured by uptake of $^3$[H]-thymidine. Daudi cells were obtained from ATCC and grown in RPMI containing 10% FCS, and 2 mM beta mercaptoethanol (media). Cells were spun and resuspended at a concentration of $1\times10^6$ cells/ml in media with added 1% human serum albumin (media & HS). To each well of a 96-well plate, 100 μl of 200 U/ml interferon α2b (Schering corporation) containing the appropriate concentration of antibody is added. 100 μl of Daudi cells in media & HS are added to the wells and the plates are incubated for 48 hours at 37° C. The plates are pulsed with 1 μCi of $^3$[H]-thymidine and incubated for an additional 24 hours. The plates are harvested, collected onto a 96-well fiber filter plate, and counted using a TopCount scintillation counter (Packard). The counts per minute were plotted as a function of antibody concentration and the data was analyzed by non-linear regression, sigmoidal dose-response (variable slope) using the Prism software (San Diego, Calif.).

In the second assay, U937 cells transfected with a construct in which an Interferon Stimulated Response Element was linked to a reporter gene (ISRE-RG) and the ability of humanized anti-IFNAR-1 antibodies to block IFN-induced expression of the reporter gene was measured. The cells were grown in RPMI containing 10% FCS, and 2 mM beta mercaptoethanol (media). The cells ($1\times10^6$ cells/ml) were resuspended in media with added 2% human serum. 100 μl of cells was added to a 96-well plate. Antibodies were serially diluted in media containing 200 U/ml of interferon α2b (Schering corporation) and 100 μl was added to each well. The plates were incubated overnight at 37° C. Following this incubation, expression of the reporter gene was assessed by flow cytometry. Geometric mean fluorescent intensity was plotted as a function of antibody concentration and the data was analyzed by non-linear regression, sigmoidal dose-response (variable slope) using the Prism software (San Diego, Calif.).

Using the above described two assays, a potency of 2-10 nM was obtained in the Daudi proliferation assay and 2-22 nM in the ISRE-RG reporter assay. The potency of the murine 64G12 was comparable to the humanized IgG1 antibodies. The results are summarized in Table 11.

TABLE 11

| | Isotype | Cell Proliferation (Daudi) $IC_{50}$ (nM) | ISRE-RG Reporter (U937) $IC_{50}$ (nM) |
|---|---|---|---|
| 64G12 | m IgG1 | 2.1 | 5.8 |
| H3K1 | h IgG4 | 9.1 | 21.5 |
| H3K1 (IgG1) | h IgG1 | 3.9 | 2.7 |
| DI M3-B K1C | h IgG1 | 10 | 4.6 |

Because the data clearly shows that the humanized anti-IFNAR-1 antibodies have potent activity with IFN alpha 2b, we tested the ability of the antibodies to inhibit IFN β responses. Two humanized antibodies tested, H3K1 (IgG1) and H3K1 (IgG4), were potent inhibitors of IFNβ induced cell signaling as measured by the reporter assay. H3K1 (IgG1) was approximately 10 times more potent than H3K1 (IgG4) while murine 64G12 was 3-fold less potent than H3K1 (IgG1). The reporter assays results for IFN-α and IFN-β are shown in the graphs of FIGS. 4A-4B.

Figure 5:
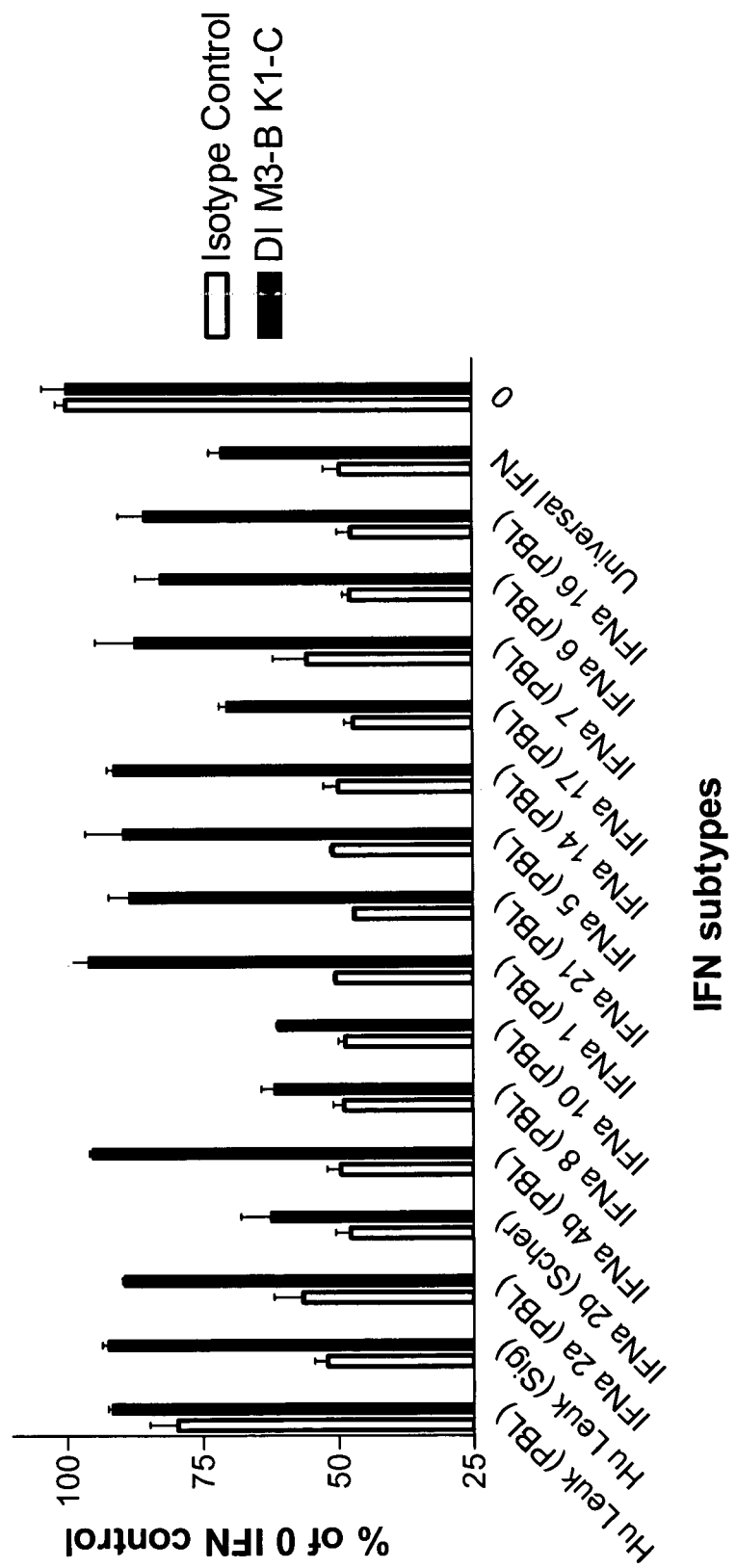
FIG. 5 is a bar graph showing reversal of the biological activity of multiple IFN alpha subtypes by a humanized anti-IFNAR-1 antibody.

To assess the ability of humanized anti-IFNAR-1 antibodies to inhibit the biological activity of multiple type I IFNs, distinct IFN alpha subtypes were tested in the Daudi proliferation assay. Daudi cells were incubated, in the presence of 10 ug/ml of the humanized antibody DI M3-B K1C or an isotype control, with one of the following IFN alpha subtypes: 2a, 2b, 4b, 8, 10, 1, 21, 5, 14, 17, 7, 6 or 16, or with either leukocyte IFN or universal IFN. Daudi proliferation was determined as described above. The results are shown in the bar graph of FIG. 5. The results demonstrate that the anti-IFNAR-1 antibody induced reversal of responses elicited by multiple type I IFNs including, but not limited to, leukocyte IFN, universal IFN, IFN α2a, α2b, α4b, α8, α10, α1, α21, α5, α14, α17, α7, α6, and α16.

EXAMPLE 7

Effects of Anti-IFNAR-1 Antibodies on Dendritic Cell Maturation

IFN alpha induces dendritic cell maturation and activation in SLE patients. An in vitro system was established to examine the ability of anti-IFNAR-1 antibodies to inhibit IFN alpha-mediated dendritic cell maturation. In these experiments, peripheral blood cells are driven toward a dendritic cell phenotype by culturing them in GM-CSF and IL-4 or GM-CSF and IFN alpha. Cultures grown in the presence of GM-CSF alone serve as a control, as these cells maintain a macrophage-like phenotype. IFN alpha drives the maturation of the dendritic cell cultures as measured by the ability of the cells to take up antigen and changes in the expression of cell surface markers.

To perform the assay, a 25 ml buffy coat was diluted four fold with PBS. The sample was separated into 4×50 ml conical tubes, and 15 ml of lymphocyte separation medium (ICN Biomedicals) was layered underneath. Following a 30-minute spin at 500×g, the buffy layer containing the PBMCs was removed and washed with PBS. Cells were resuspended in culture media at $4 \times 10^6$ cells/ml. Monocytes were isolated by incubating PBMC ($2.0 \times 10^7$ cells/5 ml/25 cm$^2$ flask) for 1.5 hrs at 37° C. in culture media and then washing away non-adherent cells twice. Following the last wash the cells were cultured in media containing an added 1% heat inactivated human serum (Gemini Bio Products). GM-CSF (500 U/ml), IL-4 (1000 U/ml), IFN alpha (IntronA; 1000 U/ml), IFNβ (1000 U/ml) and/or anti-IFNAR-1 antibody or isotype control antibody (30 ug/ml) were added to the appropriate culture flasks, and the cells were grown for three to seven days. For DC maturation, TNF-α (10 ng/ml) was added on day 3 and on day 5, the DCs were washed with PBS and treated with 1:5000 Versene for 10 minutes at 37° C. When necessary DCs were detached by gentle cell scraping, washed, and analyzed.

Each DC culture was resuspended in staining media (Hank's Balanced Salt Solution (HBSS) with 0.2% Sodium Bicarbonate, 0.01% Sodium Azide, 0.1 mM EDTA, 20 mM HEPES, and 2% FCS) and separated equally into six wells of a V-bottom 96-well plate. The cells were pulse-spun at 2100 rpm on a Sorvall RTH-750 rotor, and resuspended in 25 µl of staining media. One microgram of specific fluorochrome conjugated antibody was added to each well and incubated on ice for 45 minutes. The DCs were washed three times, resuspended in 200 µl of 2% paraformaldehyde in PBS and analyzed by flow cytometry with the Becton Dickinson FACScalibur. Gates were drawn on the Forward vs. Side Scatter graph to remove contaminating cells from the analysis.

The phenotype of DCs derived from GM-CSF in the presence of IL-4 or IFNα differs. While IL-4 derived DC express CD1a and lack CD14 and CD 123, IFNα derived DC express higher levels of CD123, and CD14 and lower levels of CD1a. In addition, IFNα-derived DCs express higher levels of costimulatory molecules MHC class II and CD86 than that found on IL-4-derived DCs. Cotreatment of the IFN cultures with the humanized anti-IFNAR1 antibody, H3K1, resulted in an expression pattern resembling that of macrophages (GM-CSF alone). Furthermore, the morphology of IFN plus H3K1 treated cultures appeared macrophage-like with a typical pancake-like appearance. Thus, this experiment demonstrated that the humanized anti-IFNAR-1 antibody is capable of inhibiting IFNα induced dendritic cell maturation. The results of the flow cytometric analysis are summarized in Table 12 (the median of the geometric mean of four experiments are shown).

TABLE 12

| Treatment | CD1a | CD123 | CD14 | CD86 | CD58 | Class II |
|---|---|---|---|---|---|---|
| GM-CSF | 42 | 135 | 427 | 172 | 208 | 123 |
| GM-CSF & IL-4 | 395 | 0.5 | 0 | 45 | 73 | 287 |
| GM-CSF & IFN | 20 | 161 | 207 | 288 | 89 | 413 |
| GM-CSF, IFN & H3K1 (IgG4) | 50 | 86 | 130 | 125 | 197 | 141 |
| GM-CSF, IFN & hIgG4 (control) | 4 | 86 | 263 | 266 | 88 | 348 |

EXAMPLE 8

Pharmacokinetics and Immunogenicity of Humanized Anti-IFNAR-1 Antibody in Rhesus Monkeys The ability of the humanized anti-IFNAR-1 antibody H3K1 to bind to peripheral blood cells from rhesus monkeys was assessed by flow cytometric analysis. The H3K1 antibody had similar reactivity with the rhesus cells as seen with the human cells, suggesting that this species is relevant for preclinical animal testing. Pharmacokinetic studies were carried out in rhesus monkeys using $^{131}$I-labeled H3K1. The half-life ($t_{1/2}\beta$) for H3K1 was ~5.5 days (2 animals), as expected for a CDR-grafted antibody in a non-human primate.

An increase in clearance rate was seen at day 10, suggested the possibility of immunogenicity. To assess this, the monkeys in the study were dosed three times with H3K1, then re-challenged with labeled antibody. A rapid clearance was observed with an estimated $t_{1/2}b$ of 14-19 hours. This result suggests that the H3K1 generated a clearing antibody response in the monkeys. The deimmunized humanized antibodies of the invention, described in the previous examples, can be used to reduce the immunogenicity of the humanized anti-IFNAR-1 antibody in vivo.

EXAMPLE 9

Neutralization of IFNAR/IFNα Activity by Humanized Anti-IFNAR-1 Antibody in Rhesus Monkeys A pharmacodynamic model was used to study the ability of the anti-IFNAR antibodies to inhibit interferon activity in vivo. In this model, exogenous IFN-α2b is dosed intramuscularly, and the activation of peripheral blood cells and the presence of serum activation markers are measured. Rhesus monkeys were treated with an i.v. infusion of 10 mg/kg murine anti-IFNAR-1 mAb 64G12, humanized anti-IFNAR-1 mAb H3K1, or vehicle control. This was followed by i.m. dose of human IFN-α2b ($3 \times 10^6$ U/Kg). Expression of the cell surface markers CD86, MHC class II, MHC class I and IFNAR1 was monitored over a 24 hour period. In addition, the plasma markers neopterin, β2 microglobulin and C-reactive protein were monitored. The major findings were: a) IFN-α2b treatment increased MHC class I expression on peripheral blood cells and the increased expression was blocked by antibody treatment, b) all three plasma markers measured were elevated by IFN-α2b treatment and H3K1 induced a 50% block in neopterin levels and a 25% reduction in CRP while no change was seen with β2 microglobulin. Therefore, a measurable in vivo response to IFNα2b was observed, which was partially blocked by antibody treatment.

Equivalents

Those skilled in the art will recognize, or be able to ascertain using no more than routine experimentation, many equivalents of the specific embodiments of the invention described herein. Such equivalents are intended to be encompassed by the following claims.

Incorporation by Reference

All patents, pending patent applications and other publications cited herein are hereby incorporated by reference in their entirety.

We claim:

1. A humanized antibody, or antigen binding fragment thereof, that specifically binds IFN alpha receptor-1, comprising:
    a heavy chain variable region comprising SEQ ID NO: 11; and
    a light chain variable region comprising SEQ ID NO: 21.

2. The humanized antibody, or antigen binding fragment thereof, of claim 1, further comprising human heavy and light constant domains.

3. The humanized antibody, or antigen binding fragment thereof, of claim 2, wherein the human heavy constant region is selected from the group consisting of human gamma 1, gamma 2, gamma 3, and gamma 4.

4. The humanized antibody, or antigen binding fragment thereof, of claim 2, wherein the human heavy constant region is gamma 1.

5. The humanized antibody, or antigen binding fragment thereof, of claim 1, wherein said humanized antibody, or antigen binding fragment thereof, comprises a substitution of alanine for phenylalanine at residue 24H utilizing the numbering system set forth in Kabat.

6. The humanized antibody, or antigen binding fragment thereof, of claim 1, wherein said humanized antibody, or antigen binding fragment thereof, comprises a substitution of methionine for leucine at residue 29H utilizing the numbering system set forth in Kabat.

7. The humanized antibody, or antigen binding fragment thereof, of claim 1, wherein said humanized antibody, or antigen binding fragment thereof, comprises a substitution of alanine for leucine at residue 29H utilizing the numbering system set forth in Kabat.

8. The humanized antibody, or antigen binding fragment thereof, of claim 1 wherein said humanized antibody, or antigen binding fragment thereof, comprises a substitution of isoleucine for valine at residue 37H and a substitution of threonine for alanine at residue 40H utilizing the numbering system set forth in Kabat.

9. The humanized antibody or, or antigen binding fragment thereof, of claim 1, wherein said humanized antibody, or antigen binding fragment thereof, comprises a substitution of proline for alanine at residue 40H utilizing the numbering system set forth in Kabat.

10. The humanized antibody, or antigen binding fragment thereof, of claim 1, wherein said humanized antibody, or antigen binding fragment thereof, comprises a substitution of lysine for arginine at residue 71H utilizing the numbering system set forth in Kabat.

11. The humanized antibody, or antigen binding fragment thereof, of claim 1, wherein said humanized antibody, or antigen binding fragment thereof, comprises a substitution of leucine for valine at residue 78H utilizing the numbering system set forth in Kabat.

12. The humanized antibody, or antigen binding fragment thereof, of claim 1, wherein said humanized antibody, or antigen binding fragment thereof, comprises a substitution of alanine for valine at residue 19L utilizing the numbering system set forth in Kabat.

13. The humanized antibody, or antigen binding fragment thereof, of claim 1, wherein said humanized antibody, or antigen binding fragment thereof, comprises a substitution of leucine for glutamine at residue 37L utilizing the numbering system set forth in Kabat.

14. The humanized antibody, or antigen binding fragment thereof, of claim 1, wherein said humanized antibody, or antigen binding fragment thereof, comprises a substitution of alanine for leucine at residue 46L utilizing the numbering system set forth in Kabat.

15. The humanized antibody, or antigen binding fragment thereof, of claim 1, wherein said humanized antibody, or antigen binding fragment thereof, comprises a substitution of isoleucine for valine at residue 58L utilizing the numbering system set forth in Kabat.

16. The humanized antibody, or antigen binding fragment thereof, of claim 1, wherein said humanized antibody, or antigen binding fragment thereof, comprises a substitution of aspartic acid for serine at residue 70L utilizing the numbering system set forth in Kabat.

17. The humanized antibody, or antigen binding fragment thereof, of claim 1, wherein said humanized antibody, or antigen binding fragment thereof, comprises a substitution threonine for phenylalanine at residue 83L utilizing the numbering system set forth in Kabat.

* * * * *